US012778699B2

(12) United States Patent
Hourtash et al.

(10) Patent No.: US 12,778,699 B2
(45) **Date of Patent: *Nov. 3, 2026**

(54) METHOD AND SYSTEM FOR COORDINATED MULTIPLE-TOOL MOVEMENT USING A DRIVABLE ASSEMBLY

(71) Applicant: Intuitive Surgical Operations, Inc., Sunnyvale, CA (US)

(72) Inventors: Arjang M. Hourtash, Sunnyvale, CA (US); Probal Mitra, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/265,751

(22) Filed: Jul. 10, 2025

(65) Prior Publication Data

US 2025/0339224 A1 Nov. 6, 2025

Related U.S. Application Data

(63) Continuation of application No. 18/010,242, filed as application No. PCT/US2021/047374 on Aug. 24, 2021, now Pat. No. 12,396,816.

(Continued)

(51) Int. Cl.

*A61B 34/37* (2016.01)
*A61B 34/00* (2016.01)

(Continued)

(52) U.S. Cl.

CPC .............. *A61B 34/37* (2016.02); *A61B 34/20* (2016.02); *A61B 34/75* (2016.02);

(Continued)

(58) Field of Classification Search

CPC ......... A61B 34/37; A61B 34/20; A61B 34/75; A61B 2034/2059; A61B 2034/2065;

(Continued)

(56) References Cited

U.S. PATENT DOCUMENTS 8,004,229 B2 * 8/2011 Nowlin .................. B25J 9/1689 318/568.2
2009/0248037 A1 * 10/2009 Prisco .................... A61B 34/71 606/130

(Continued)

FOREIGN PATENT DOCUMENTS

WO WO-2015142947 A1 * 9/2015 ......... A61B 1/00149
WO WO-2016069659 A1 5/2016
WO WO-2018013979 A1 1/2018

OTHER PUBLICATIONS

International Preliminary Reporton Patentability for Application No. PCT/US2021/047374 mailed Mar. 9, 2023, 14 pages.

(Continued)

*Primary Examiner* — Adam R Mott
*Assistant Examiner* — James Miller Watts, III
(74) *Attorney, Agent, or Firm* — Osha Bergman Watanabe & Burton LLP

(57) ABSTRACT

A robotic system includes a manipulator assembly and a processing system. The manipulator assembly includes a first manipulator, a second manipulator, and a drivable structure. The first manipulator and the second manipulator are mechanically coupled to the drivable structure. The processing system is configured to determine a drivable structure motion for effecting a commanded motion for a first end effector of a first tool mechanically coupled to the first manipulator. Performing only the drivable structure motion would cause motion of the first end effector simultaneously with motion of a second end effector, the second end effector being of a second tool mechanically coupled to the second manipulator. The processing system is further (Continued)

configured to determine a movement of the second manipulator and the second tool that, when performed simultaneously with the drivable structure motion, would compensate for the motion of the second end effector.

20 Claims, 12 Drawing Sheets

Related U.S. Application Data

(60) Provisional application No. 63/071,971, filed on Aug. 28, 2020.

(51) Int. Cl.
*A61B 34/20* (2016.01)
*A61B 34/30* (2016.01)

(52) U.S. Cl.
CPC ................. *A61B 2034/2059* (2016.02); *A61B 2034/2065* (2016.02); *A61B 2034/306* (2016.02)

(58) Field of Classification Search
CPC .............. A61B 2034/306; A61B 34/32; A61B 2034/305; A61B 2090/067; B25J 9/0087; B25J 9/1676; B25J 9/1682; G05B 2219/39391; G05B 2219/40609
See application file for complete search history.

(56) References Cited

U.S. PATENT DOCUMENTS

| | | | | |
|---|---|---|---|---|
| 2010/0274087 | A1 * | 10/2010 | Diolaiti .................. | A61B 34/37 600/407 |
| 2010/0332033 | A1 | 12/2010 | Diolaiti et al. | |
| 2013/0144307 | A1 * | 6/2013 | Jeong ..................... | A61B 90/10 606/130 |
| 2014/0276952 | A1 * | 9/2014 | Hourtash ............... | A61B 34/37 700/263 |
| 2016/0120611 | A1 * | 5/2016 | Lohmeier .............. | A61B 90/50 606/130 |
| 2017/0333141 | A1 * | 11/2017 | Itkowitz ................. | A61G 13/02 |
| 2019/0231460 | A1 * | 8/2019 | DiMaio .................. | A61B 50/13 |
| 2020/0146769 | A1 * | 5/2020 | Eyre ...................... | A61G 13/06 |
| 2020/0289217 | A1 * | 9/2020 | Denlinger .............. | A61B 34/74 |
| 2023/0263585 | A1 | 8/2023 | Hourtash et al. | |

OTHER PUBLICATIONS

International Search Report and Written Opinion for Application No. PCT/US2021/047374, mailed Dec. 8, 2021, 19 pages.
Vertut, J., and Coiffet, P., "Robot Technology: Teleoperation and Robotics Evolution and Development." English translation, Prentice-Hall, Inc., Inglewood Cliffs, NJ, USA 1986, vol. 3A, 332 pages.

* cited by examiner

METHOD AND SYSTEM FOR COORDINATED MULTIPLE-TOOL MOVEMENT USING A DRIVABLE ASSEMBLY

CROSS-REFERENCE TO RELATED APPLICATIONS

This application is a continuation of and claims the benefit of priority under 35 U.S.C. § 120 to U.S. patent application Ser. No. 18/010,242, filed Dec. 14, 2022, which is a National Stage Entry of PCT/US2021/047374 filed Aug. 24, 2021, which claims priority to and the benefit of the filing date of U.S. Provisional Patent Application 63/071,971, filed on Aug. 28, 2020, which are hereby incorporated by reference herein in their entirety.

BACKGROUND

Field of Invention

The present invention generally provides improved robotic and/or medical (including surgical) devices, systems, and methods.

Overview

A robotic system can be used to perform a task at a worksite. For example, robotic systems may include one or more manipulator arms, each manipulator arm including a manipulator configured to couple to tools (also called "instruments") for performing the task. A manipulator arm may include two or more links coupled together by one or more joints. Joints may be active joints that are actively moved by the robotic system. Joints may also be passive joints that are not actively moved by the robotic system. A joint may have one or more degrees of freedom, and may be, as example, a revolute joint, a prismatic joint, a ball joint, or a complex joint with more complex motion. The configuration of a manipulator arm and the tool(s) coupled to the manipulator arm may be determined by the positions the one or more joints of the manipulator arm, by the geometric design of the manipulator arm, including that of the one or more links and one or more joints of the manipulator arm, and as applicable considerations such as mechanical elasticity of the manipulator arm.

Example robotic systems include industrial and recreational robotic systems. Example robotic systems also include medical robotic systems used in procedures for diagnosis, non-surgical treatment, surgical treatment, etc. As a specific example, robotic systems include minimally invasive, robotic telesurgical systems in which surgeons may operate on patients from bedside or remote locations. Telesurgery refers generally to surgery performed using surgical systems where the surgeon uses some form of remote control to manipulate surgical tools rather than directly holding and manipulating the tools by hand. A robotic medical system usable for telesurgery or other telemedical procedures may include a remotely controllable robotic manipulator arm with a teleoperable manipulator. Operators of the robotic medical system may remotely control motion of the remotely controllable manipulator arm. Operators may also manually move pieces of the robotic medical system into positions or orientations within its environment.

Multiple tools may be supported by a drivable structure of a robotic system. Movement of the drivable structures may be used to effect movement of one of the tools. However, when multiple tools are supported by a drivable structure, movement of the drivable structure arm may result in movement of all tools supported by the drivable structure.

For these and other reasons, it would be advantageous to provide improved devices, systems, and methods for robotic applications, including industrial, recreational, medical, and other robotic applications.

SUMMARY

In general, in one aspect, one or more embodiments relate to a robotic system comprising: a manipulator assembly comprising: a first manipulator; a second manipulator; a drivable structure, wherein the first manipulator is mechanically coupled to the drivable structure, and wherein the second manipulator is mechanically coupled to the drivable structure; and a processing system configured to perform operations comprising: receiving a first command from an input device, the first command indicating a first commanded motion for a first end effector of a first tool mechanically coupled to the first manipulator, wherein the first manipulator and the first tool together comprise a plurality of first links coupled by a plurality of first joints, determining a first movement for effecting the first commanded motion, the first movement comprising a first relative motion of the first end effector relative to the drivable structure and a drivable structure motion of the drivable structure, wherein performing only the drivable structure motion would cause a first caused motion of the first end effector simultaneously with a second caused motion of a second end effector, the second end effector being of a second tool mechanically coupled to the second manipulator, wherein the second manipulator and the second tool together comprise a plurality of second links coupled by a plurality of second joints, determining a second movement of the plurality of second joints, wherein performing the second movement simultaneously with the drivable structure motion would compensate for the second caused motion and maintain a state of the second end effector, and driving the manipulator assembly to simultaneously perform the first and second movements.

In general, in one aspect, one or more embodiments relate to a robotic system comprising: a drivable assembly comprising: a first drivable structure configured to support and move a first tool; a second drivable structure configured to support and move a second tool, the second tool comprising an imaging device, wherein the second drivable structure and the second tool together comprise a plurality of second links coupled by a plurality of second joints; a third drivable structure mechanically coupled to the first drivable structure and mechanically coupled to the second drivable structure, such that moving the third drivable structure moves proximal portions of the first and second drivable structures; and a processing system configured to perform operations comprising: receiving a command from an input device, the command indicating a commanded motion for a first end effector of the first tool relative to an imaging reference frame of the imaging device, determining a first movement of the drivable assembly for effecting the commanded motion, the first movement comprising a third drivable structure motion of the third drivable structure, determining a second movement of the plurality of second joints to compensate for an effect of the third drivable structure motion on the imaging reference frame and maintain a state of the imaging reference frame relative to a world reference frame, and driving the drivable assembly to simultaneously perform the first and second movements.

In general, in one aspect, one or more embodiments relate to a method for operating a robotic system, the robotic system comprising a manipulator assembly, the manipulator assembly comprising: a first manipulator, a second manipulator, a drivable structure, wherein the first manipulator is mechanically coupled to the drivable structure, and wherein the second manipulator is mechanically coupled to the drivable structure, and the method comprising: receiving a first command from an input device, the first command indicating a first commanded motion for a first end effector of a first tool mechanically coupled to the first manipulator, wherein the first manipulator and the first tool together comprise a plurality of first links coupled by a plurality of first joints; determining a first movement for effecting the first commanded motion, the first movement comprising a first relative motion of the first end effector relative to the drivable structure and a drivable structure motion of the drivable structure, wherein performing only the drivable structure motion would cause a first caused motion of the first end effector simultaneously with a second caused motion of a second end effector, the second end effector being of a second tool mechanically coupled to the second manipulator, wherein the second manipulator and the second tool together comprise a plurality of second links coupled by a plurality of second joints, determining a second movement of the plurality of second joints, wherein performing the second movement simultaneously with the drivable structure motion would compensate for the second caused motion and maintain a state of the second end effector, and driving the manipulator assembly to simultaneously perform the first and second movements.

In general, in one aspect, one or more embodiments relate to

A method for operating a robotic system, the robotic system comprising a drivable assembly, the drivable assembly comprising: a first drivable structure configured to support and move a first tool; a second drivable structure configured to support and move a second tool, the second tool comprising an imaging device, wherein the second drivable structure and the second tool together comprise a plurality of second links coupled by a plurality of second joints, a third drivable structure mechanically coupled to the first drivable structure and mechanically coupled to the second drivable structure, such that moving the third drivable structure moves proximal portions of the first and second drivable structures; and the method comprising: receiving a command from an input device, the command indicating a commanded motion for a first end effector of the first tool relative to an imaging reference frame of the imaging device, determining a first movement of the drivable assembly for effecting the commanded motion, the first movement comprising a third drivable structure motion of the third drivable structure, determining a second movement of the plurality of second joints to compensate for an effect of the third drivable structure motion on the imaging reference frame and maintain a state of the imaging reference frame relative to a world reference frame, and driving the drivable assembly to simultaneously perform the first and second movements.

Other aspects of the invention will be apparent from the following description and the appended claims.

DETAILED DESCRIPTION

Figure 1:
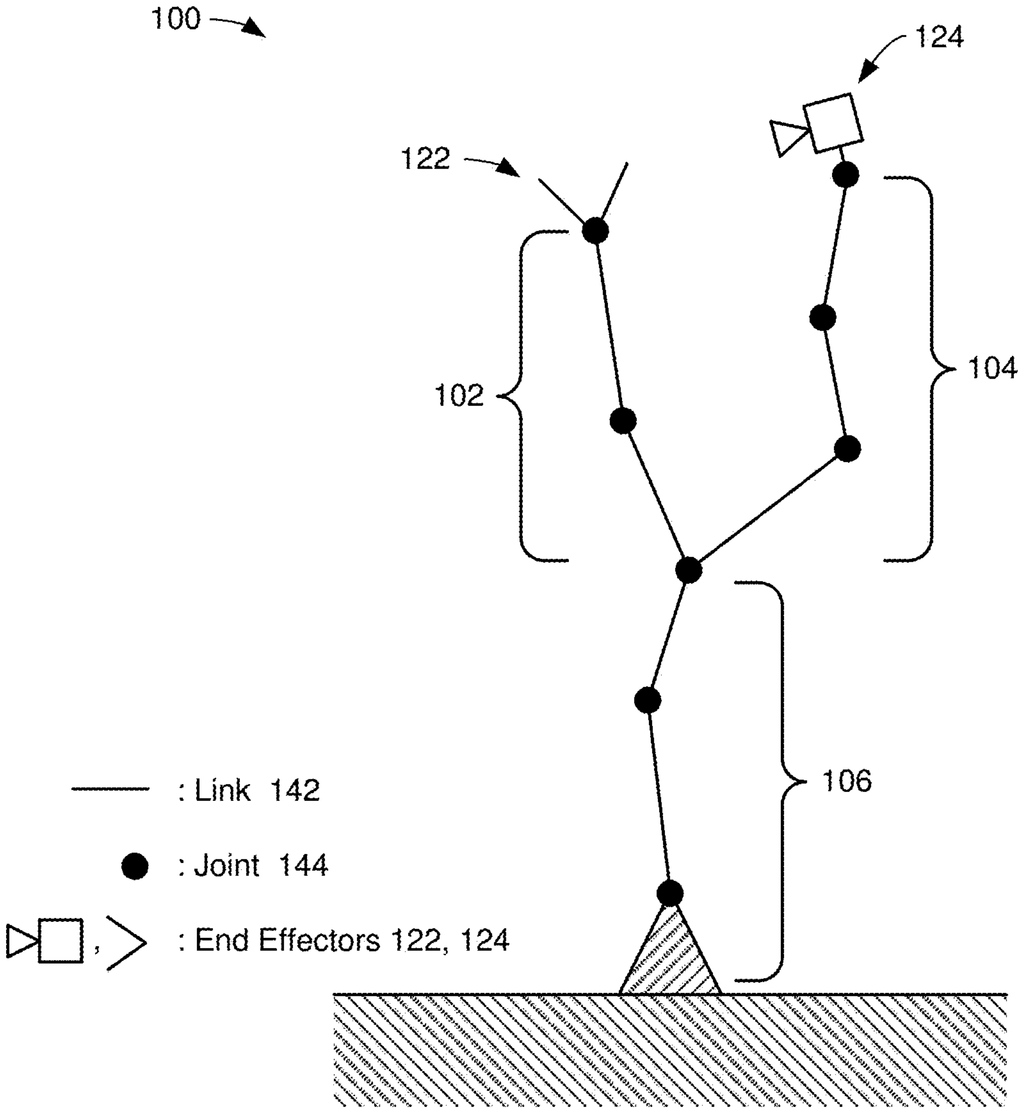
FIG. 1 diagrammatically shows a drivable assembly in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

Embodiments of the disclosure facilitate movement of a tool by a drivable assembly. The drivable assembly may include a third drivable structure, and multiple other drivable structures mechanically coupled to the third drivable structure, such that movement of the third drivable structure moves the other drivable structures. For example, the drivable assembly may include a manipulator assembly, the first and second drivable structures may include first and second manipulators, and the first and second manipulators may be mechanically coupled to a third drivable structure of the manipulator assembly. In some embodiments, the third drivable structure includes a third manipulator movable by actuators that drive the third manipulator.

As a specific example, a drivable assembly may include a manipulator assembly including a drivable structure, and multiple manipulators mechanically coupled to the drivable structure. The drivable structure may be driven and moved by actuators of the manipulator assembly. The drivable structure may include a manipulator-supporting link that physically couples to the manipulators. The manipulators may be configured to support tools. Accordingly, a tool supported by a manipulator may be moved by moving one or more joints of the tool, or by moving a part of the manipulator assembly proximal to the tool. For example, the tool may be moved through motion of the manipulator supporting the tool, by motion of part or all of the drivable structure, or by motion of the entire manipulator assembly. Motion of the drivable structure may be caused by movement of one or more joints of the drivable structure, by movement of one or more joints of the manipulator assembly proximal to the drivable structure, or by movement of the entire manipulator assembly itself (e.g., if the manipulator assembly is disposed on or includes a wheeled cart, or is slidably mounted to a railing of a table, floor, or ceiling, the entire manipulator assembly may be translated and/or rotated). Thus, the movement of an end effector of the tool may be effected partially or entirely through motion of the drivable structure. Moving the drivable structure to move the tool may be beneficial, for example to provide additional degrees of freedom or increased range of motion to the tool. For example, a first tool supported by a first manipulator of the manipulator assembly may have fewer degrees of freedom or lesser range of motion as compared to another tool, which can make using the first tool more cumbersome, or can even limit the first tool's ability to reach certain locations of a work site. The degrees of freedom or range of motion may be limited for various reasons. For example, a variety of different tools may have different structures and designs that provide different degrees of freedom or ranges of motion.

Referring now to the drawings, in which like reference numerals represent like parts throughout the several views, FIG. 1 as a particular example shows a drivable assembly (100) that may include a third drivable structure (106), physically supporting a first drivable structure (102) and a second drivable structure (104). The first drivable structure (102) may be configured to support a first tool (122), and the second drivable structure may be configured to support a second tool (124). Each of the first, second, and third drivable structures (102, 104, 106) and the first and second tools (122, 124) may include any number of joints (144) of any type, and any number of links (142) of any geometry. While FIG. 1 shows a third drivable structure (106) supporting two drivable structures (102, 104) configured to support two tools (122, 124), the third drivable structure (106) may support any number of drivable structures, and the first and second drivable structures (102, 104) may each support any number of tools.

In the embodiment shown in FIG. 1, the combination of the first tool (122) and the first drivable structure (102) has fewer joints than the combination of the second tool (124) and the second drivable structure (104). In one example, described in detail below, with reference to various figures, the second tool (124) supported by the second drivable structure (104) may include shaft offset joints to enable a translational offset along the shaft of the second tool (124), and the first tool (122) on the first drivable structure (102) may not include shaft offset joints. Thus, the end effector of the second tool (124) may have more degrees of freedom or a larger range of motion than the end effector of the first tool (122). To facilitate increased workspace of the first tool (122), the first tool (122) may be moved by movement of the third drivable structure (106). However, movement of the third drivable structure (106) would also result in caused motion of the second drivable structure (104) and the second tool (124). In one or more embodiments, compensatory movements are determined by a processing system and performed by the second drivable structure (104) and/or the second tool (124) to partially or entirely cancel the motion of the end effector of the second tool (124) that would otherwise result due to the movement of the third drivable structure (106). In some embodiments, one or more additional drivable structures configured to support tools are also mechanically coupled to, and distally located from, the third drivable structure (106); additional compensatory motions for these additional drivable structures (and any additional tools supported by such additional drivable structures) are also determined by the processing system and performed by these additional drivable structures. Robotic systems supporting those and other additional features, and methods enabling these features are discussed further in the following description. While FIG. 1 schematically shows a drivable assembly in general terms, more specific examples are subsequently described with reference to FIG. 2A, FIG. 2B, and FIG. 3, showing different embodiments.

Figure 2A:
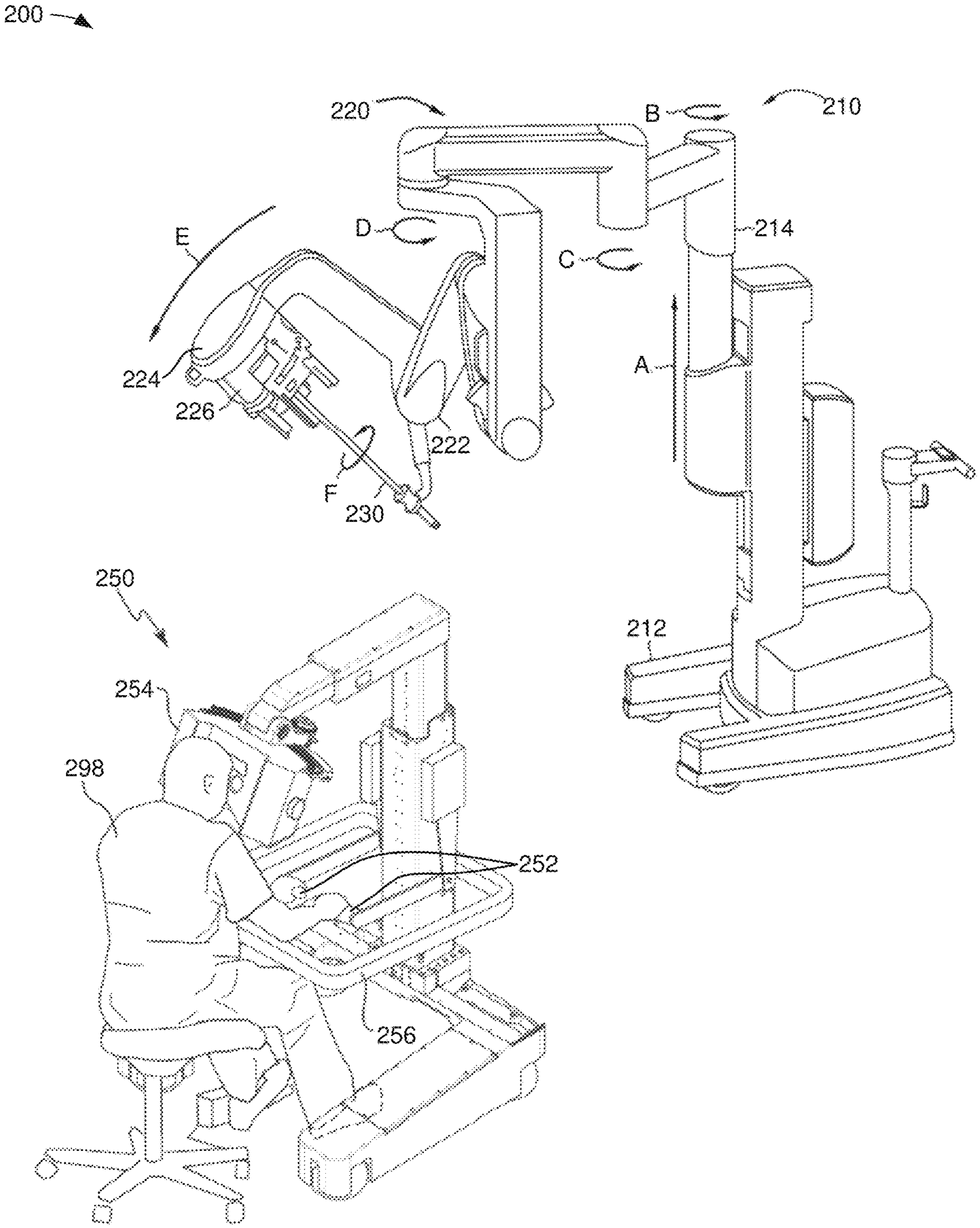
FIG. 2A shows an example of a teleoperated robotic system in accordance with one or more embodiments.
Figure 2B:
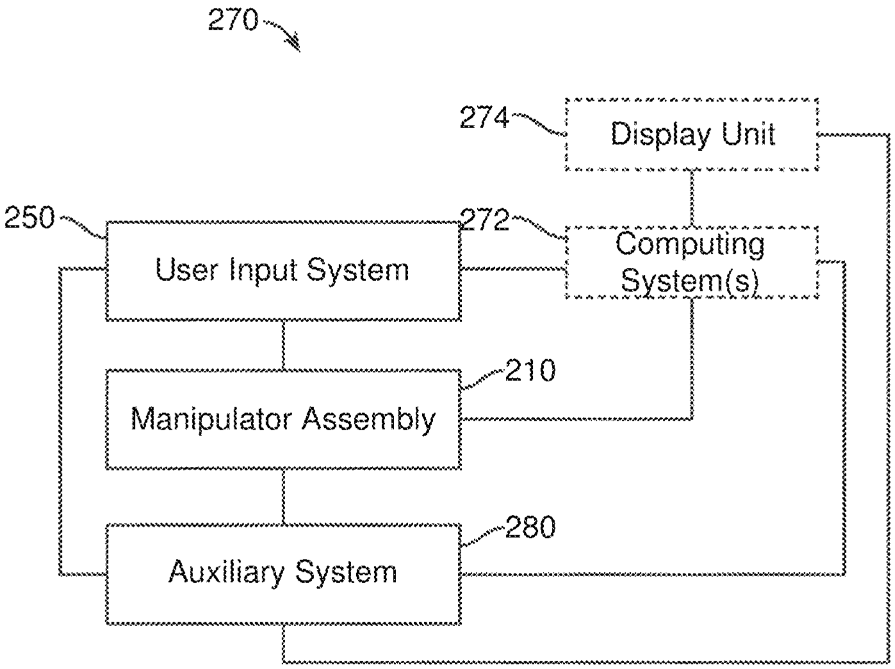
FIG. 2B diagrammatically shows various components of the teleoperated robotic system of FIG. 1A, in accordance with one or more embodiments.
Figure 3:
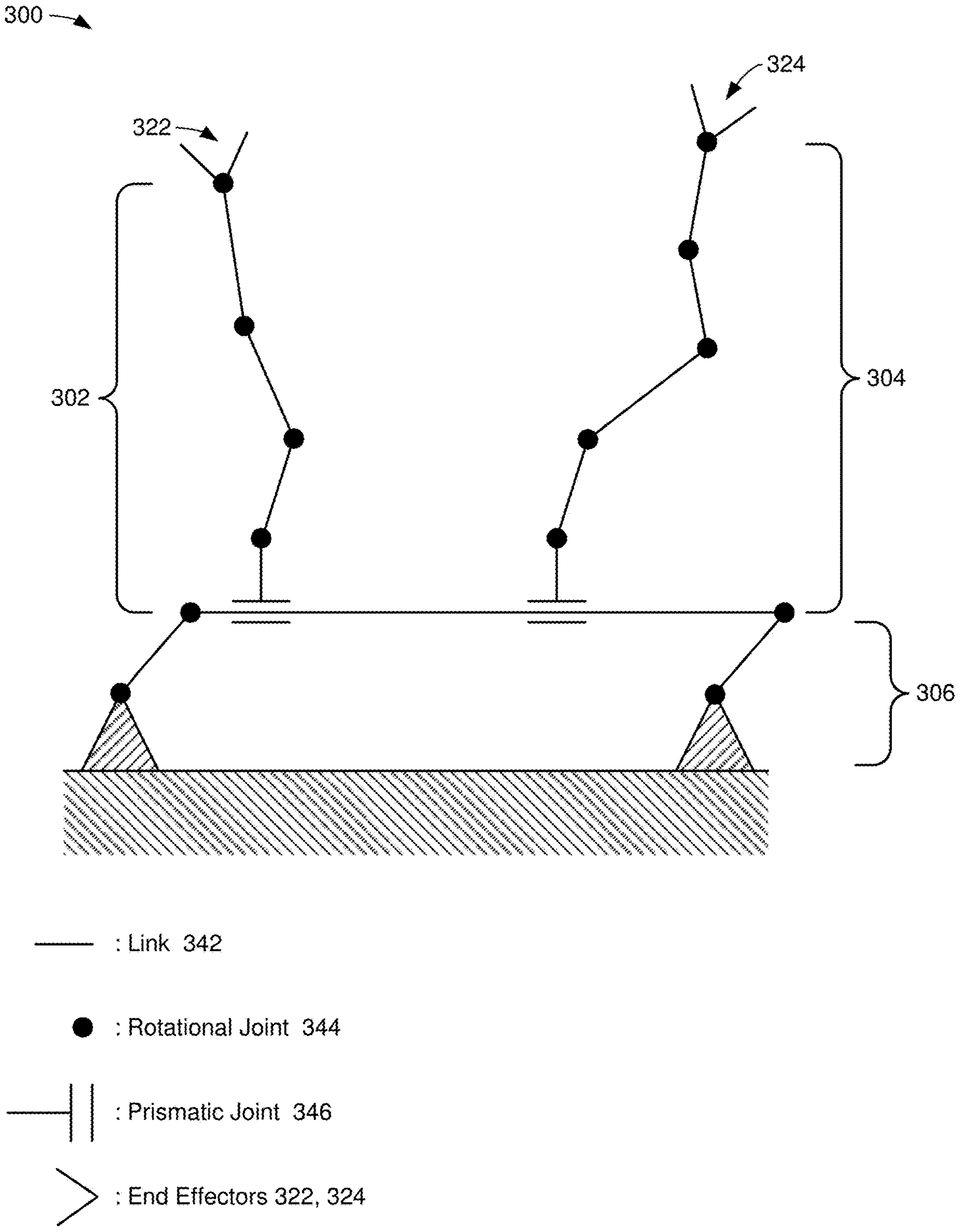
FIG. 3 shows an example of a robotic manipulator assembly, in accordance with one or more embodiments.

Turning to FIG. 2A an example of a robotic system (200), in accordance with one or more embodiments, is shown. The robotic system (200), in the example of FIG. 2A, includes a robotic manipulator assembly (also "manipulator assembly") (210) and a user input system (250). In a teleoperation scenario, an operator (298) may use the user input system (250) to operate the manipulator assembly (210), such as in a leader-follower configuration (also often called teleoperation configuration or master-slave configuration in industry) of the robotic system (200). In the leader-follower configuration, the user input system (250) is the leader, and the manipulator assembly (210) is the follower of the leader-follower configuration.

The manipulator assembly (210) may be used to introduce a set of tools (not shown here, discussed below with reference to FIGS. 4A and 4B) to a work site through a single port (230) (a cannula is shown) inserted in an aperture. In a medical scenario, the work site may be on or within a body cavity of a patient, and the aperture may be a minimally invasive incision or a natural body orifice. The port (230) may be a structure held by a drivable structure (222) at a manipulator-supporting link (224) of the drivable structure (222). The drivable structure (222) may be coupled to additional joints and links (214, 220) of the manipulator assembly, and these additional joints and links (214, 220) may be mounted on a base (212). The drivable structure (222) may terminate in the manipulator-supporting link (224). A set of manipulators (226) may couple to the manipulator-supporting link (224). Each of the manipulators (226) may include a carriage (or other tool-coupling link) configured to couple to a tool, and each of the manipulators (226) may include one or more joint(s) that can be driven to move the carriage. For example, a manipulator (226) may include a prismatic joint that, when driven, linearly moves the carriage and any tool(s) coupled to the carriage. This linear motion may be along an insertion axis, as further described below with reference to FIG. 4A and FIG. 4B.

The additional joints and additional links (214, 220) may be used to position the port (230) at the aperture or another location. FIG. 2A shows a prismatic joint for vertical adjustment (as indicated by arrow "A") and a set of rotary joints for horizontal adjustment (as indicated by arrows "B" and "C"). The drivable structure (222) is used to robotically pivot the port (230) (and the tools disposed within it at the time) in yaw, pitch and roll angular rotations about the remote center as indicated by arrows D, E and F, respectively.

Actuation of the degrees of freedom provided by joint(s) of the tool(s) may be provided by actuators disposed in, or whose motive force (e.g., linear force or rotary torque) is transmitted to, the tool(s). Examples of actuators include rotary motors, linear motors, solenoids, etc. The actuators may drive transmission elements in the manipulators and/or in the tools to control the degrees of freedom of the tool(s). For example, the actuators may drive rotary discs of the manipulator that couple with rotary discs of the tool(s), where driving the rotary discs of the tools drives transmission elements in the tool that couple to move the joint(s) of the tool, or to move the end effector(s) of the tool, as further discussed below with reference to FIG. 4A and FIG. 4B. Accordingly, the degrees of freedom of the tool(s) may be controlled by actuators that drive the tool(s) in accordance with control signals determined based on inputs from the associated input devices (e.g., input devices (252) of the user input system (250)). The control signals may be determined to cause tool motion or other actuation as indicated by movement of the input control devices or any other control signal. Furthermore, appropriately positioned sensors, e.g., encoders, potentiometers, etc., may be provided to enable measurement of indications of the joint positions, or other data that can be used to derive joint position, such as joint velocity. The actuators and sensors may be disposed in, or transmit to or receive signals from, the manipulator(s) (226).

While a particular configuration of the manipulator assembly (210) is shown in FIG. 2A, those skilled in the art will appreciate that embodiments of the disclosure may be used with any design of manipulator assembly. For example, a manipulator assembly may have any number and any types of degrees of freedom, may or may not be configured to couple to a port, or use a port other than a cannula, unlike what is shown in FIG. 2A, etc.

In the example shown in FIG. 2A, the user input system (250) includes one or more input devices (252) operated by the operator (298). In the example shown in FIG. 2A, the one or more input devices (252) are contacted and manipulated by the operator's (298) hands, with one input device for each hand. Examples of such hand-input-devices include any type of device manually operable by human user, e.g., joysticks, trackballs, button clusters, and/or other types of haptic devices typically equipped with multiple degrees of freedom. Position, force, and/or tactile feedback devices (not shown) may be employed to transmit position, force, and/or tactile sensations from the tools back to the operator's hands through the input devices (252).

The input devices (252) are supported by the user input system (250) and are shown as mechanically grounded, and in other implementations may be mechanically ungrounded. An ergonomic support (256) may be provided in some implementations; for example, FIG. 2A shows an ergonomic support (256) including forearm rests on which the operator (298) may rest his or her forearms while manipulating the input devices (252). In some examples, the operator (298) may perform tasks at a work site near the manipulator assembly (210) during a medical procedure by controlling the manipulator assembly (210) using the input devices (252).

A display unit (254) is included in the user input system (250). The display unit (254) may display images for viewing by the operator (298). The display unit (254) may provide the operator (298) with a view of the worksite with which the manipulator assembly (210) interacts. The view may include stereoscopic images or three-dimensional images to provide a depth perception of the worksite and the tool(s) of the manipulator assembly (210) in the worksite. The display unit (254) may be moved in various degrees of freedom to accommodate the operator's viewing position and/or to provide control functions. Where a display unit (such as the display unit (254) is also used to provide control functions, such as to command the manipulator assembly, the display unit also includes an input device (e.g. another input device (252)).

When using the user input system (250), the operator (298) may sit in a chair or other support in front of the user input system (250), position his or her eyes to see images displayed by the display unit (254), grasp and manipulate the input devices (252), and rest his or her forearms on the ergonomic support (256) as desired. In some implementations, the operator (298) may stand at the workstation or assume other poses, and the display unit (254) and input devices (252) may differ in construction, be adjusted in position (height, depth, etc.), etc.

FIG. 2B diagrammatically shows a system (270). The system (270) may correspond to the robotic system (200) and may include one or more computing systems (272). A computing system (272) may include a processing system, and be used to process input provided by the user input system (250), e.g., from the input device(s) (252) manipulated by an operator. A computing system (272) may further be used to provide an output, e.g., a video image to the display unit (274). Examples of display unit (274) include LCDs, LEDs, organic LED displays, projectors, etc. One or more computing systems (272) may further be used to control the manipulator assembly (210).

In one or more embodiments, the computing system(s) (272) executes control methods. The control methods may include instructions for controlling one or more components of the manipulator assembly (210). In one or more embodiments, joint movements of the manipulator assembly (210) are controlled by control methods driving one or more joints using actuators of the manipulator assembly (210), the joint movements being calculated by a processor of a processing system of the computing system(s) (272). The control methods may process control signals from the user input system (250) or elsewhere, and/or sensor signals (e.g., positional encoder data from joint position sensors, image data from image tools such as ultrasonic probes or cameras or endoscopes, etc.), to calculate commands for the joint actuators.

The control methods may perform at least some of the calculations of the joint commands using vectors and/or matrices, some of which may have elements corresponding to positions, velocities, and/or forces/torques of the joints. The range of alternative joint configurations available to the control methods may be conceptualized as a joint space. The joint space may, for example, have as many dimensions as the manipulator assembly has degrees of freedom, and a particular configuration of the manipulator assembly may represent a particular point in the joint space, with each coordinate corresponding to a joint state of an associated joint of the manipulator assembly.

As used herein, the term "state" of a joint or multiple joints refers to the control variables associated with the joint or the multiple joints, respectively. For example, the state of an angular joint may refer to the angle defined by that joint within its range of motion, and/or to the angular velocity (or speed or direction) of the joint. Similarly, the state of an axial or prismatic joint may refer to the joint's axial or linear position, and/or to its axial or linear velocity (or speed or direction). While one or more of the control methods described herein include position controllers, they often also have velocity control aspects. Alternative embodiments may rely primarily or entirely on velocity controllers, force controllers, acceleration controllers, etc. without departing from the disclosure. Many aspects of control systems that may be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control technique, a velocity control technique, an acceleration control technique, a force or torque control technique, a combination of some or all of the foregoing, etc.

Multiple control modes may further exist. For example, during a robotic task being performed under the control of input devices (252) operated by a user, various joints of the manipulator assembly may be position-controlled. However, in another control mode, one or more of the joints may be "floating", allowing an operator or assistant to readily externally articulate these one or more floating joints. A floating joint facilitates motion of that joint due to externally applied force. For example, a joint held in place by a brake may be floated by partially or entirely releasing the brake; an example of such a joint includes a passive joint held in place by an electromagnetic brake. As another example, a joint that is driven to move by actuator(s) may be held in place by the actuator(s), and floated by updating the command to the actuator(s) to the current position or velocity or acceleration.

A floating joint is thus readily reconfigured by an externally applied force or torque, without a control algorithm and/or a braking force seeking to counteract the reconfiguration caused by sufficient externally applied force or torque. Additionally or alternatively, a floating joint may also be controlled to impose other characteristics, such as a certain level of damping. Multiple control modes may be combined during operation of the manipulator assembly, e.g., some joints may be controlled to resist or rebound from external articulation of those joints, while other joints may be floating and facilitate external articulation of those other joints. Parameters such as joint position, velocity, or acceleration of the joints may be detected by joint sensors. The sensor signals may be used to provide kinematic information of the manipulator assembly. A floating joint may still be braked, actuated, or otherwise managed for friction or gravity compensation; the compensation, for example, may be provided by passive springs, actively driven actuators, etc. Further, in some embodiments, joints that are not moved by actuators may still be gravity compensated, friction compensated, dampened, etc. by actuators.

The architecture of the control methods used for controlling the manipulator assembly may be of any appropriate form. As a specific example, the control architecture may be hierarchical, and may include a high-level controller and multiple joint controllers. A commanded movement may be received by the high-level controller in, for example, a Cartesian-coordinate space (referred to herein as Cartesian-space). The commanded movement may be, for example, based on a movement command (e.g., in the form of a position and/or velocity) received from the user input system (250), or any other system that provides a movement command. The commanded movement may be converted into commanded joint positions or joint velocities (e.g., linear or angular joint positions, linear or angular joint velocities). The conversion may be performed using an inverse kinematics algorithm. Subsequently, the joint controllers may convert the received commanded joint positions or velocities into commanded currents to drive the actuators producing joint movements. The joint movements together may produce a manipulator assembly movement that reflects the commanded movement.

In one embodiment of the disclosure, a joint controller controls a joint position. Alternatively, the joint controller may control other variables such as joint velocity, joint force (linear force or angular torque). A joint controller may receive a feedback signal in the form of a sensed joint state from an associated joint sensor, which it can use for closed-loop control. The sensed joint state may include a joint position, a joint velocity (or component of velocity such as speed or direction), and/or a joint acceleration (or component of acceleration), etc., representing the joint movement. The sensed joint state may be derived from signals obtained from a joint sensor. Such a sensor may include, for example, an encoder, a potentiometer, an accelerometer, a hall effect sensor, etc. A state observer or estimator (not shown) may be used. Each joint controller may implement any appropriate control scheme, such as a proportional integral derivative (PID), proportional derivative (PD), full state feedback, sliding mode, or various other control schemes, without departing from the disclosure.

In one or more embodiments, the control methods further perform at least one of the steps described in FIG. 6, FIG. 7A, FIG. 7B, FIG. 7C, or 7D. These methods may be used to drive one or more of the actuators of the manipulator assembly (210).

A computing system (272) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities. A computer processor of a computing system (272) may be an integrated circuit for processing instructions. For example, the computer processor may be one or more cores or micro-cores of a processor. A communication interface of a computing system (272) may include an integrated circuit for connecting the computing system (272) to a network (not shown) and/or to another device, such as another computing system (272). Further, the computing system (272) may include one or more output devices, such as a display unit (274), a printer, a speaker, external storage, or any other output device. Software instructions in the form of computer readable program code to perform embodiments of the disclosure may be stored, in whole or in part, temporarily or permanently, on non-transitory computer readable medium. Specifically, the software instructions may correspond to computer readable program code that, when executed by a processor(s), is configured to perform one or more embodiments of the invention. A computing system (272) may be connected to or be a part of a network. The network may include multiple nodes. Each node may correspond to a computing system, or a group of nodes.

The manipulator assembly (210) may couple to a tool including an imaging device, e.g., an endoscope or an ultrasonic probe, to capture images of the worksite and output the captured images to an auxiliary system (280). The auxiliary system (280) may process the captured images in a variety of ways prior to any subsequent display. For example, the auxiliary system (280) may overlay the captured images with a virtual control interface prior to displaying the combined images to the operator via the user input system (250). One or more separate display units (274) may also be coupled with a computing system (272) and/or the auxiliary system (280) for local and/or remote display of images, such as images of the procedure site, or other related images.

Turning to FIG. 3, an example of a drivable structure assembly (300), in accordance with one or more embodiments, is shown. The drivable structure assembly (300) includes a third drivable structure (306), physically supporting a first drivable structure (302) and a second drivable structure (304). The first drivable structure (302) may support a first tool (322), and the second drivable structure may support a second tool (324). In various embodiments, the drivable structure assembly (300) includes a manipulator assembly, with the first drivable structure (302) including a first manipulator and the second drivable structure (304) including a second manipulator. Each of the first, second, and third drivable structures (302, 304, 306) and the first and second tools (322, 324) may each include any number of joints (344, 346) of any type, and any number of links (342) of any geometry. In one embodiment, the drivable structure assembly (300) is part of a medical robotic system.

The drivable structure assembly (300) may be configured as a tableside-installed medical robotic system. For example, the third drivable structure (306) may be attached to a base of a surgical or examination table. As indicated in FIG. 3, the third drivable structure may provide a movable support for the first and second drivable structures (302, 304). Prismatic joints (346) may enable translational movement of the first and the second drivable structures (302, 304) relative to the third drivable structure (306). While two drivable structures (the first and the second drivable structures (302, 304)) are shown in FIG. 3, any number of drivable structures may be supported by the third drivable structure (306). Further, the medical robotic system may include one or more additional drivable structure assemblies with the same or a different design. For example, the drivable structure assembly (300) may be installed on one side of the table, and a same or different manipulator assembly may be installed on the same side, or another side, of the table.

Figure 4A:
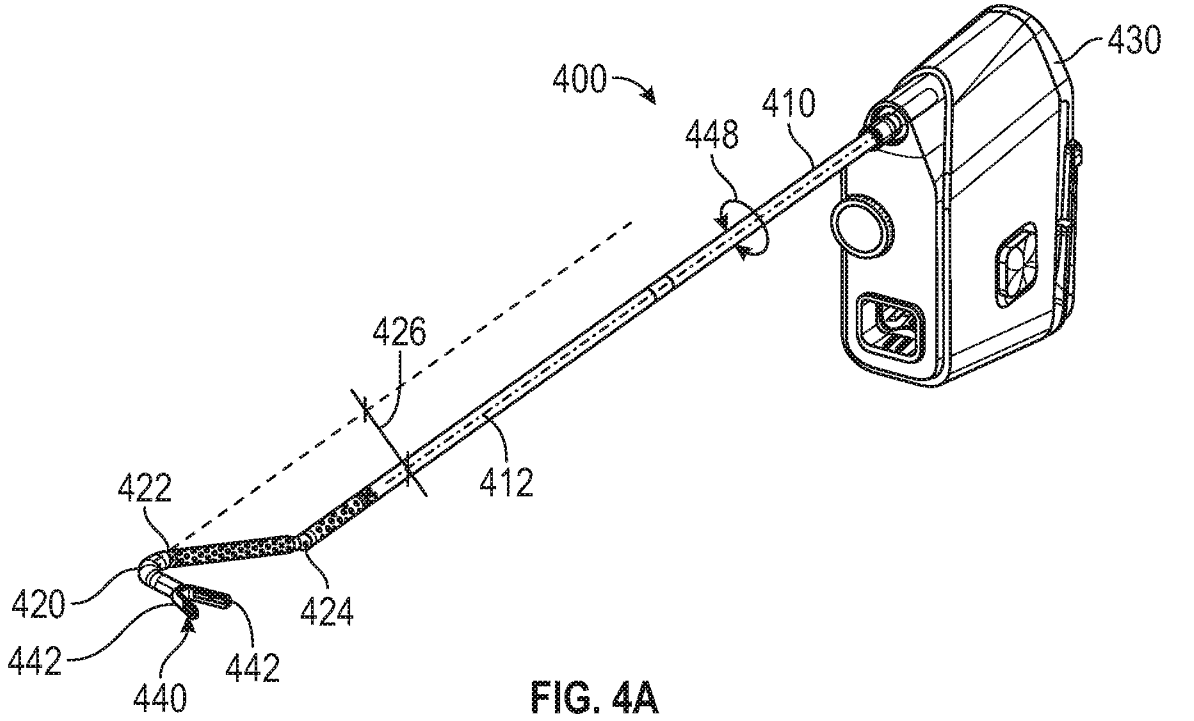
FIG. 4A shows an example of a tool with shaft offset joints, in accordance with one or more embodiments.
Figure 4B:
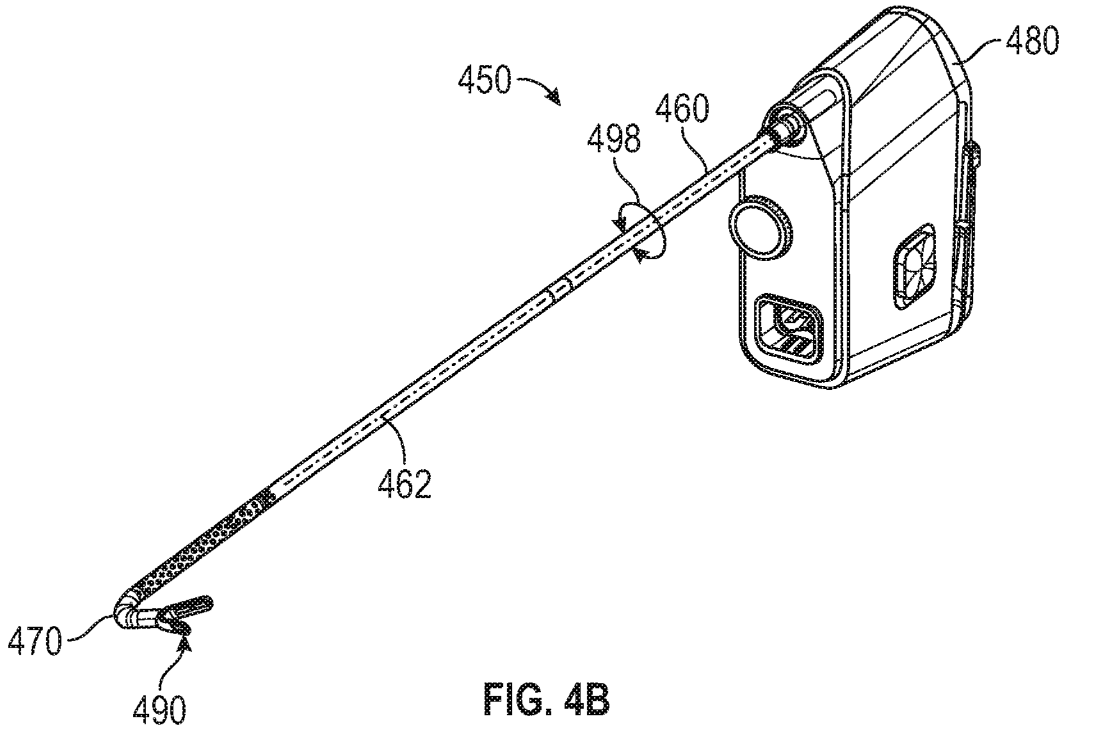
FIG. 4B shows an example of a tool without shaft offset joints, in accordance with one or more embodiments.

Turning to FIG. 4A and FIG. 4B, examples of tools (400, 450) (also called instruments (400, 450)) are shown. Tools (400, 450) may be used for robotic procedures such as robotic medical procedures (e.g. surgeries), in accordance with one or more embodiments.

The tool (400) in FIG. 4A includes a shaft (410), and an end effector located at a first end of the tool (400). A housing (430), arranged to releasably couple the tool (400) to a manipulator (shown, for example, in FIG. 2A), is located at a second end of the tool (400). The shaft (410) may be rotatably coupled to the housing (430) to enable angular displacement of the shaft (410) relative to the housing (430), as indicated by arrows (448).

Various types of end effectors (440) exist. For example, the end effector (440) may include one finger, two fingers (e.g., jaws (442) that may open and close), or three or more fingers. Examples of end effectors include, but are not limited to, scissors, forceps, staplers, etc. As another example, an end effector may further include an imaging device, e.g., an endoscope or an ultrasonic probe, to capture images of the worksite. The end effector may be actuated by transmission elements (e.g., cables, metal bands, screws, tubes, push rods, etc.) that connect parts of the tool to drive elements (e.g., pulleys, capstans, spools, nuts, linear slides, or the like) (not shown) in the housing (430). Movement (e.g. translation or rotation) of the drive elements may thus control the position of the end effector, or other degrees of freedom such as jaw opening, such that the end effector may translate or rotate, the jaws may open and close, etc. Upon coupling of the tool (400) on a drivable structure such as a manipulator, the drive elements may engage with actuators of the drivable structure, such as by engaging with transmission elements coupled to the actuators. As an example, a description of the control of a tool like the tool (400) may be found in U.S. Pat. No. 6,394,998, entitled "Surgical Tools for Use in Minimally Invasive Telesurgical Applications."

In the example shown in FIG. 4A, the joints of the tool (400) include a wrist (420) proximal to the end effector (440) and two shaft offset joints (422, 424) proximal to the wrist (420). The wrist (420) may enable rotation of the end effector (440) in one or more direction. The shaft offset joints (422, 424) may enable, for example, a translational offset (426) of the end effector (440) relative to the insertion axis (412), in addition to the rotating provided by the wrist (420). The shaft offset joints (422, 424) may, thus, increase the workspace reachable by the end effector (440) of the tool (400). Like the end effector (440), the wrist (420) and the shaft offset joints (422, 424) may be actuated by control cables.

The tool (450) shown in FIG. 4B includes various elements of the tool (400) shown in FIG. 4A and may operate in a substantially similar manner to the tool (400) shown in FIG. 4A. Specifically, the tool (450) includes a shaft (460) and a wrist (470) proximal to an end effector (490). Further, the tool (450) has an insertion axis (462) for insertion/retraction of the tool (450). The tool (450) also allows angular displacement of the shaft (460) relative to the housing (480) as indicated by the arrows (498). Unlike the tool (400) in FIG. 4A, the tool (450) is not equipped with shaft offset joints. Accordingly, the tool (450) cannot achieve a translational offset of the end effector (440) relative to the insertion axis (462) as can the tool (400). The shaft (460) without shaft offset joints may be made more rigid, may be configured to allow the transmission of higher forces or torques, or may be configured to transmit forces and torques with reduced friction, as compared to a similar shaft including shaft offset joints (e.g. shaft (410)). An example of tool that generally utilizes transmission of a higher forces compared to other tools is a tissue stapler.

Also, in various implementations, a tool without shaft offset joints may be less costly, easier to service, maintain and/or clean than a comparable tool with shaft offset joints.

While FIG. 4A and FIG. 4B show particular configurations of tools, designed to engage with a particular type of manipulator, other configurations of tools are within the scope of the disclosure. For example, embodiments of tools (400, 450) may have multi-degree-of-freedom wrists (e.g., pitch and yaw degrees of freedom), single-degree-of-freedom wrists (e.g., pitch or jaw), or no wrists. Also, embodiments of tools (400, 450) may have any type of end effector (440, 490) including, for example, scissors, forceps, staplers, irrigation nozzles, hooks, scissors, blunt dissection tools, needle drivers, imaging devices, or the like. Further, different housings (430, 480) may be used to interface with different types of manipulators.

Figure 5B:
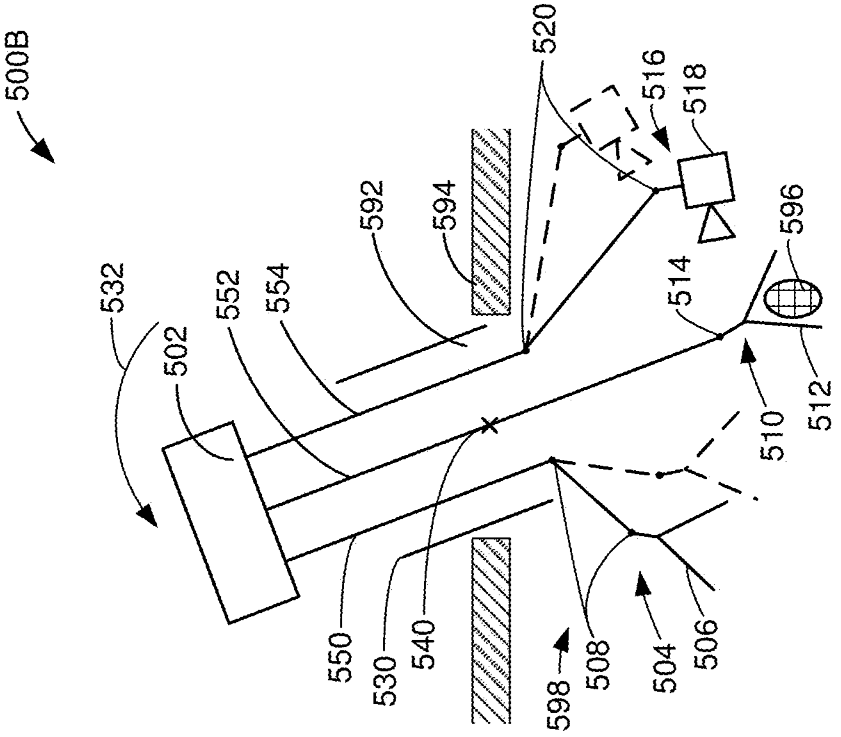
FIG. 5A and FIG. 5B schematically show an example of repositioning a tool using a movement of a drivable structure supporting multiple tools, in accordance with one or more embodiments.
Figure 5A:
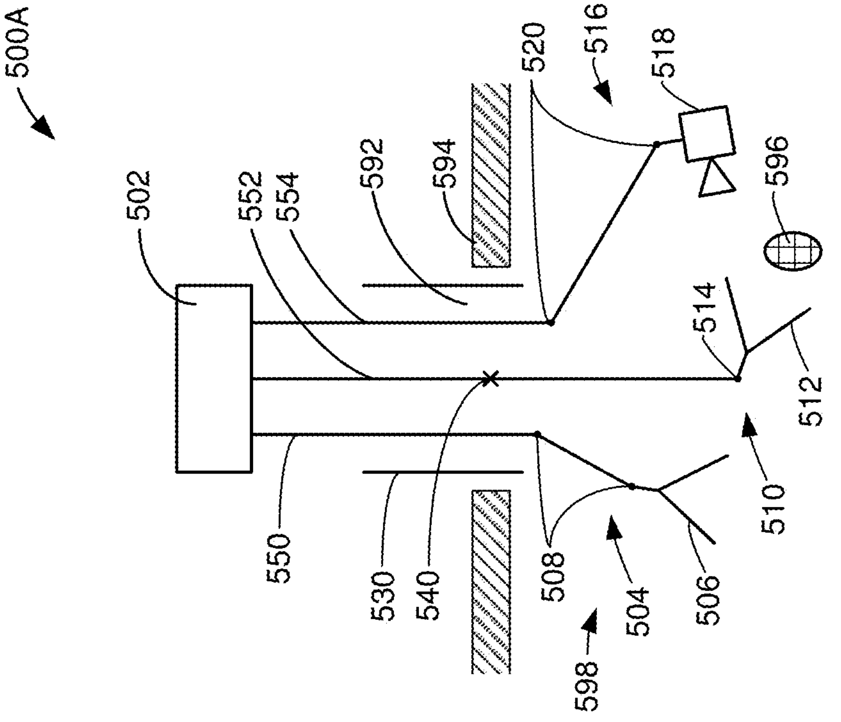

FIG. 5A and FIG. 5B schematically illustrate a repositioning of an end effector of a tool using a movement of a drivable structure proximal to the tool and other tools, in accordance with one or more embodiments. FIG. 5A shows a scenario (500A) before the repositioning, and FIG. 5B shows a scenario (500B) after the repositioning.

Specifically, FIG. 5A and FIG. 5B show a drivable structure assembly including a manipulator assembly, where a drivable structure including a manipulator-supporting link (502), supports multiple manipulators (550, 552, 554) coupled to multiple tools (504, 510, 516). In other words, the manipulator-supporting link (502) forms a common mechanical base for the manipulators (550, 552, 554) that support the tools (504, 510, 516). The manipulator-supporting link (502) may correspond to the manipulator-supporting link of a drivable structure as previously introduced with reference to FIG. 2A. Movement of one or more joints of the drivable structure, for example, may result in movement of the manipulator-supporting link (502). When the manipulator-supporting link (502) is moved, the portions of the manipulators (550, 552, 554) attached to the manipulator-supporting link (502) are also moved. If the manipulators (550, 552, 554) are held fixed in configuration, then the movement of the manipulator-supporting link (502) also moves tools (504, 510, 516).

Repositioning of a tool (e.g. tool 504, 510, or 516) through movement of a common mechanical base such as the manipulator-supporting link (502) may be used to increase the degrees of freedom and/or the range of motion of a tool (e.g. tool 504, 510, or 516). Consider, for example, the tool (510) in FIG. 5A. The tool (510) is equipped with an end effector (512). Assume that the end effector (512) interacts with the target (596) in a procedure. For example, assume that an operator remotely controls the end effector (512) of tool (510) by providing a commanded motion via the input devices (252) in FIG. 2A. In the example of FIG. 5A and FIG. 5B, the operator may provide commands intended to cause the end effector (512) to interact with the target (596). The target (596) may be any kind of object, and the tool (510) may be any kind of tool, equipped with an end effector suitable to interact with the target (596). For example, in a surgical scenario, the end effector may include forceps, and the target may include tissue.

In the configuration shown in FIG. 5A, the end effector (512) is unable to reach the target (596) if the manipulator-supporting link (502) does not move relative to the target (596). One factor contributing to the inability of the end effector (512) to reach the target (596) is that the tool (510) has fewer joints as compared to some other tools. For example, tool (510) lacks shaft offset joints while tools (504, 516) include shaft offset joints (508, 520). If tools (510, 504, 516) are identical except that tool (510) lacks shaft offset joints, then tools (504) and (516) generally have increased number of degrees of freedom and/or an increased range of motion in comparison to tool (510). However, even if tool (510) includes additional joints such as shaft offset joints or other joints, end effector (512) may still be unable to reach target (596) without motion of the manipulator-supporting link (502) if the additional joints do not provide sufficient additional range of motion.

In the example of FIG. 5A and FIG. 5B, the end effector of tool (516) includes an imaging device (518). The imaging device (518) is configured to capture and provide images for display to an operator of the tools (504, 510). Where the tools (504, 510) are visible within these images, the images provide visual feedback that can be used by the operator of the tools (504, 510) in controlling the tools (504, 510). In the example of FIG. 5A and FIG. 5B, the tools (504, 510, 516) are inserted through a cannula (530) toward a work site (598) containing the target (596); the cannula (530) is inserted through an aperture (592) in the barrier (594). In a medical scenario, the barrier (594) may be a body wall of a patient, and the aperture (592) may be a minimally invasive incision or a natural body orifice of the patient.

FIG. 5B illustrates a pivoting motion (532) about a remote center of motion (540) (also called "remote center" (540)) about which portions of the manipulator assembly pivots. In the example shown in FIG. 5B, the manipulator assembly has been positioned, and/or is controlled, such that the remote center (540) is located approximately centrally in the aperture (592). As shown in the example of FIG. 5B, movement of the manipulator-supporting link (502) relative to the target (596), such as the pivoting motion (532) or some other movement (e.g. translational movement, combined translational and rotational movement, etc.), may enable the end effector (512) to execute a commanded motion indicated by the operator via the input devices (252) that the end effector (512) may not have been able to otherwise execute.

In one or more embodiments, the movement (e.g. pivoting motion (532)) moves the manipulator-supporting link (502) supporting the manipulators (550, 552, 554) supporting tools (504, 510, 516). If the manipulators (550, 552, 554) are held static relative to the manipulator-supporting link (502), then the tools (504, 510, 516) jointly move in a common motion in response to the movement of the manipulator-supporting link (502) (all pivoting about the remote center (540) with the pivoting motion (532)). Thus, the pivoting motion (532), if the manipulators are held static relative to the manipulator-supporting link (502), would cause caused motion of the end effectors (512) of the tool (510) such that it reaches the position shown in FIG. 5B, and would also cause motion of the end effectors (506, the end effector including imaging device (518)) of the tools (504, 516) such that the tools (504, 516) to reach the position shown by dashed lines in FIG. 5B, if these caused motions are uncompensated. In the example shown in FIG. 5B, the movement of tool (510) is commanded and thus is desired, but the movement of tools (504, 516) that would result from performing only the pivoting motion (532), may not be commanded, expected, or desired. For example, tools (504, 516) may be expected to remain stationary, in absence of movement commands. Alternatively, tools (504, 516) may be expected to follow commands provided for these tools, independent from the movement of tool (510).

In one or more embodiments, the manipulators (550, 552, 554) supporting the tools (504, 516) are driven to move in a manner that compensates partially or entirely for the motion caused by the movement of the manipulator-supporting link (502) (e.g. pivoting motion (532)). The compensation may involve movement of one or more joints of the manipulators (550, 552, 554) supporting the tools (504, 516), and/or one or more joints of the tools (504, 516). For example, the compensation may involve moving the shaft offset joints (508, 520) or other joints of the tools (504, 516), and/or moving the manipulators (550, 554) to perform an insertion or retraction movement along the insertion axes of the tools (504, 516). The compensation may be performed such that the end effectors (506, the end effector including imaging device (518)) remain substantially stationary within the work site, while the end effector (512) of the tool (510) is repositioned relative to the work site. Example methods performed to enable the operations discussed with reference to FIG. 5A and FIG. 5B are provided below in the form of flowcharts.

In the above discussion, the distinction between tools (504, 516), and tool (510) is that tool (510) have fewer joints (e.g. lack shaft offset joints or other joints). However, more generally, tool (510) may have the same or a greater number of joints, the same or a greater number of degrees of freedom, or the same or a greater range of motion as compared to other tools supported by the manipulators (550, 554) coupled to manipulator-supporting link (502). In all of these cases, movement of the manipulator-supporting link (502) can help increase the degrees of freedom and/or the range of motion of a tool such as tool (510) (or of another tool coupled distally to the manipulator-supporting link, including tools (504, 516) or some other tool). Further, while FIG. 5A and FIG. 5B illustrate a pivoting motion (532) in conjunction with the work site being accessible through an aperture, the described methods apply to any type of movement and are not limited to a pivoting. For example, the movement of the manipulator-supporting link (502) may alternatively be or include one or more other rotational movements, linear or nonlinear translational movements, combinations of translational and rotational movements, etc.

While FIG. 1, FIG. 2A, FIG. 2B, FIG. 3, FIG. 4A, FIG. 4B, FIG. 5A, and FIG. 5B show various configurations of components, other configurations may be used without departing from the scope of the disclosure. For example, various components may be combined to create a single component. As another example, the functionality performed by a single component may be performed by two or more components. Further, while the components are often described in context of medical scenarios such as surgical scenarios, embodiments of the disclosure may be equally applicable to other domains that involve robotic manipulation, e.g., non-surgical scenarios or systems, non-medical scenarios or systems, etc.

The methods used to perform the described movements and compensations are subsequently described with reference to the flowcharts of FIG. 6, FIG. 7A, FIG. 7B, FIG. 7C, and FIG. 7D. Broadly speaking, the methods, in accordance with one or more embodiments, apply to any type of drivable assembly, i.e., configurations of mechanically connected drivable structures as previously introduced. Such a drivable assembly may include a first drivable structure and a second drivable structure, both mechanically disposed on a third drivable structure. More than two drivable structures may be disposed on the third drivable structure. The first drivable structure, the second drivable structure (and any additional drivable structure, if existing), may each support a tool.

The methods used to perform the described movements and compensations may have various applications. For example, these methods may facilitate use of tools with fewer joints compared to other tools used simultaneously (e.g. lack shaft offset joints as schematically illustrated in FIG. 5A and FIG. 5B). The use of the described technique in this disclosure, however, are not limited to tools that lack shaft offset joints or tools with fewer joints compared to other tools. For example, the technique described for moving a tool may be used to increase the reachable workspace of the tool, to increase the degrees of freedom or range of motion of the tool, to avoid obstacles, etc., regardless of how many or what joints the tool has. The technique described in this disclosure may also be used to increase the degrees of freedom and range of motion of tools that have the same or a greater number of joints, degrees of freedom, range of motion, etc. Accordingly, the described technique may generally increase the versatility of a robotic system.

FIG. 6, FIG. 7A, FIG. 7B, FIG. 7C, and FIG. 7D show flowcharts in accordance with one or more embodiments. The flowcharts of FIG. 6, FIG. 7A, FIG. 7B, FIG. 7C, and FIG. 7D depict methods for a coordinated multiple tool movement using drivable assembly movement, in accordance with one or more embodiments. One or more of the steps in FIG. 6, FIG. 7A, FIG. 7B, FIG. 7C, and FIG. 7D may be performed by various components of the systems, previously described with reference to FIG. 1, FIG. 2A, FIG. 2B, FIG. 3, FIG. 4A, FIG. 4B, FIG. 5A, and FIG. 5B.

The subsequently described methods are not limited to a particular configuration of drivable structures, tools and/or degrees of freedom. Instead, the methods are applicable to any combination of distal drivable structures coupled to a common proximal drivable structure, and used in any type of scenario. For example, the described methods are applicable to any of the configurations shown in FIG. 1, FIG. 2A, FIG. 2B, FIG. 3, FIG. 4A, and FIG. 4B.

While the various steps in these flowcharts are presented and described sequentially, one of ordinary skill will appreciate that some or all of the steps may be executed in different orders, may be combined or omitted, and some or all of the steps may be executed in parallel. In addition, additional steps may further be performed. Furthermore, the steps may be performed in response to a triggering event (e.g. polling, interrupt, certain sensor input, etc.) or performed without the need for specific triggering events (e.g. passage of time, completion of a previous process, etc.). Accordingly, the scope of the disclosure should not be considered limited to the specific arrangement of steps shown in FIG. 6, FIG. 7A, FIG. 7B, FIG. 7C, and FIG. 7D.

Figure 6:
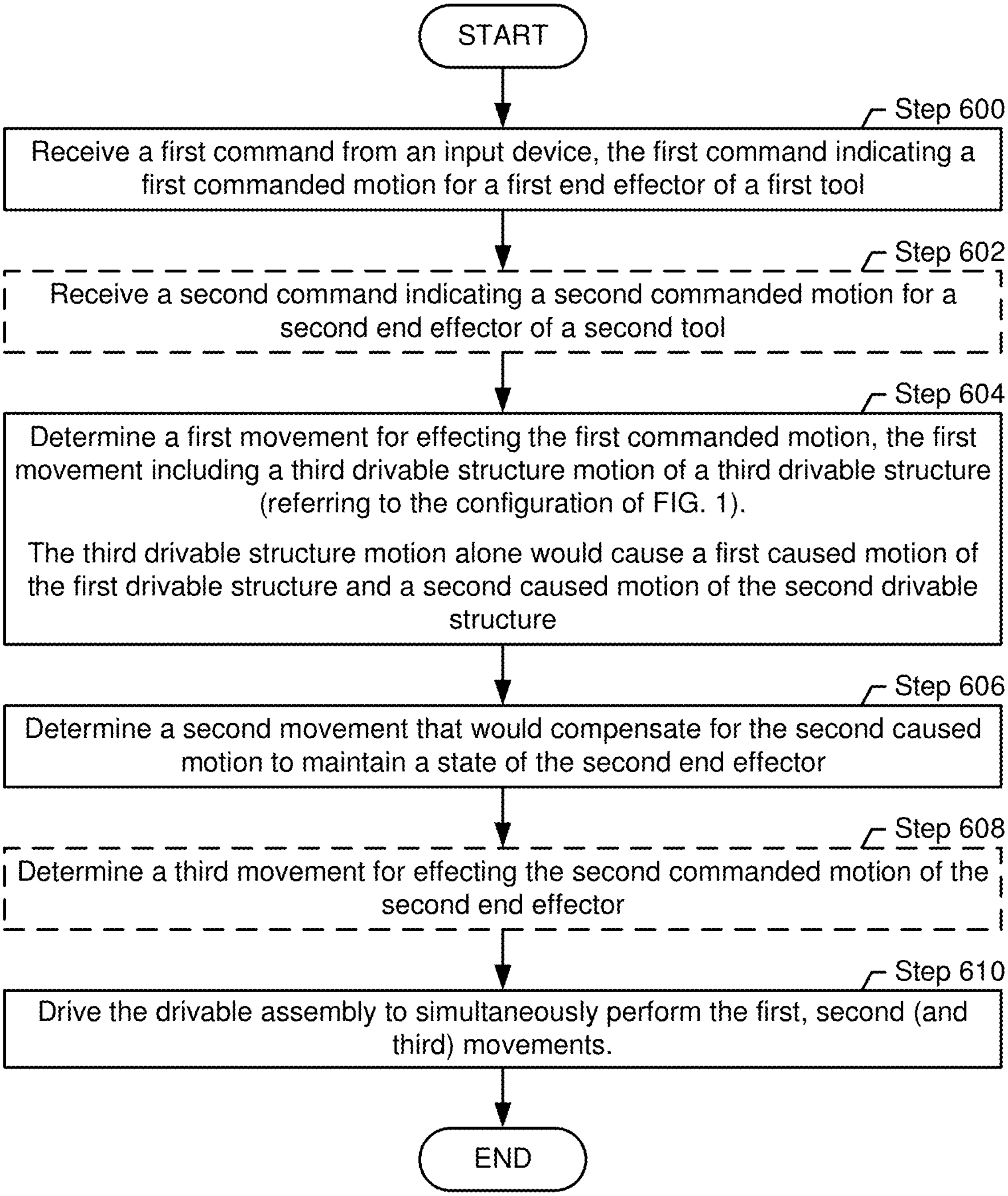
FIG. 6 shows a flowchart describing a method for coordinated multiple-tool movement using a robotic system, in accordance with one or more embodiments.

The flowchart of FIG. 6 may be understood as a first flowchart describing the steps associated with a coordinated multiple-tool movement using a drivable assembly. FIG. 7A, FIG. 7B, FIG. 7C, and FIG. 7D describe additional aspects. As discussed earlier, some of the described steps, or some of these additional aspects, may or may not be included in a specific implementation.

Turning to the flowchart of FIG. 6, a method for coordinated multiple-tool movement using a drivable assembly, in accordance with one or more embodiments, is shown. Broadly speaking, the method may be executed to control joint configurations of a drivable assembly, based on one or more commands received from one or more input devices. The drivable assembly may be, for example, the manipulator assembly described with reference to FIG. 2A, or any other drivable assembly, including drivable assemblies configured to support more than two end effectors. The commands may be for controlling the state (e.g., position, orientation, velocity, and/or acceleration) of one or more end effectors supported by the drivable assembly. Referring to the drivable assembly (100) of FIG. 1, a third drivable structure motion is used to cause movement of the first end effector, supported by the first drivable structure. The third drivable structure motion would also cause potentially unwanted motion of the second end effector supported by the second drivable structure, if the caused motion of the second drivable structure is uncompensated. The method computes and causes compensatory movements to reduce or prevent the potentially unwanted motion of the second end effector. Additional movements of the second drivable structure and/or the tool including the second end effector may be superimposed to move the second end effector according to another command, e.g., a commanded motion of the second end effector provided by the user.

In this discussion of FIG. 6, the first, second, and third drivable structures may be of any configuration (e.g., with any number of joints of any type and/or any number of links of any geometric configuration). The first and second drivable structures may support first and second tools, respectively, of any type. The steps and methods are applicable to various embodiments, including the embodiments described in this disclosure. To aid explanation, the steps are described using terminology that refers to the examples provided in FIG. 1, and further illustrated by being also described with regard to specific embodiments, such as those provided in FIG. 2A or FIG. 5A-5B.

In Step 600, a first command is received, for example, from an input device, or from another external or internal source. For example, the first command may be a user input, or it may be internally produced by an autonomous or semi-autonomous algorithm controlling the operation of the drivable assembly. The first command may indicate a first commanded motion for the first end effector of the first tool. The first commanded motion may specify any motion parameter, such as translational or rotational positions and/or velocities and/or accelerations, e.g., in the form of a trajectory of the first end effector. The first commanded motion may include various components. For example, the first commanded motion may be for repositioning and/or reorienting the first end effector. In addition, the first commanded motion may also involve other components such as opening/closing jaws of the first end effector (if applicable) or otherwise operating the first end effector. In one or more embodiments, the first commanded motion is provided relative to an imaging reference frame of an imaging device. The imaging device, as further discussed below, may be included in the second end effector of a second tool supported by the drivable assembly, as illustrated in FIG. 1. A discussion of reference frames is provided below with reference to FIG. 8.

In Step 602, a second command is received. Similar to the first command, the second command may be from an input device or any other external or internal source. The second command may indicate a second commanded motion of a second end effector of a second tool. The second commanded motion may specify a motion parameter, e.g., in the form of a trajectory of the second end effector. The second commanded motion may include various components, just as the first commanded motion may include various components. In one or more embodiments, the second commanded motion is provided relative to an imaging reference frame of an imaging device. The existence and execution of Step 602 is optional. Additional commands may optionally be received for additional end effectors of additional tools.

In Step 604, a first movement for effecting the first commanded motion of the first end effector is determined. In one or more embodiments, and referring to FIG. 1, the first movement includes a third drivable structure motion of the third drivable structure. In the example of FIG. 5A and FIG. 5B, the drivable structure motion may be the motion of the manipulator-supporting link (502). The drivable structure motion may be obtained by executing control methods as previously described with reference to FIG. 2B. For example, the first commanded motion may be processed by an inverse kinematics algorithm to obtain joint positions (e.g., joint angles for rotary joints) for the joints associated with the drivable structure.

The third drivable structure motion causes a first caused motion of the first drivable structure. Because at least a second drivable structure is disposed on the drivable structure, performing the third drivable structure motion would also result in a second caused motion of the second drivable structure (and of a second end effector of a tool supported by the second drivable structure), if the third drivable structure motion is the only motion performed. In an embodiment, the end effector of the second tool includes a manipulation tool and no imaging device. In another embodiment, the end effector of the second tool includes the imaging device. Where the second tool includes an imaging device with the imaging reference frame and the first movement is performed relative to the imaging reference frame, performing only the third drivable structure motion would move the first end effector simultaneously with moving the imaging reference frame.

As a specific example, when performing Step 604 for the embodiment shown in FIG. 2A, the first commanded motion causes a first movement. The first movement includes a drivable structure motion. Movement of the drivable structure, if performed in isolation (without an additional compensatory movement) would cause a first caused motion of the first end effector disposed on the first manipulator, simultaneously with a second caused motion of the second end effector disposed on the second manipulator. In one or more embodiments, the first movement further includes a relative motion of the first end effector relative to the drivable structure. The relative motion of the first end effector may be an insertion/retraction of the first tool along the insertion axis of the first tool, an opening/closing of the first end effector of the first tool, a pivoting of the first end effector (e.g., at the wrist) of the first tool, or any other actuation of the first end effector.

In Step 606, a second movement to compensate for the second caused motion is determined to maintain a state (e.g., a position and/or orientation, or a linear or angular velocity or acceleration) of the second end effector. The second movement may be obtained by executing control methods as previously described with reference to FIG. 1B. For example, the first commanded motion may be processed by an inverse kinematics algorithm to obtain joint positions (e.g., joint angles for rotary joints) for the joints involved in the second movement.

As a specific example in reference to FIG. 1, which shows an imaging device as the second end effector, the second movement compensates for the effect of the third drivable structure motion on the imaging reference frame relative to a world reference frame. Accordingly, when performing the second movement simultaneously with the third drivable structure motion, the state of the imaging reference frame relative to the world reference frame would be partially or wholly maintained. In other words, the imaging reference frame (position and/or orientation) would remain stationary in the world reference frame. The second movement may involve movement of a set of joints, the set of joints including one or more joints of the second drivable structure and the second tool.

As a specific example in reference to FIG. 2A, the second movement compensates for the second caused motion to maintain the state of the second end effector, when the second movement is executed simultaneously with the drivable structure motion. The second movement may involve a set of joints, including joints of the second manipulator and the second tool.

Now referring to the examples shown in FIG. 4A, FIG. 5A, and FIG. 5B, the set of joints involved in the second movement may include the shaft offset joints, a joint providing insertion/retraction along the insertion axis, and/or another joint.

Step 606 may optionally be performed for additional drivable structures and end effectors disposed on the third drivable structure.

In Step 608, a third movement for effecting the second commanded motion of the second end effector is determined. The third movement, when superimposed on the first movement and the second movement, may effect the second commanded motion. The third movement may be obtained by executing control methods as previously described with reference to FIG. 2B. For example, the second commanded motion, obtained in Step 602, may be processed by an inverse kinematics algorithm to obtain joint positions (e.g., joint angles for rotary joints) for the set of joints including joints of the second manipulator and the second tool. The existence and execution of Step 608 is optional. Specifically, the execution of Step 608 may be performed following Step 602. While Step 608 is described for the second end effector, it may also be applicable to any additional end effector to be controlled.

In Step 610, the drivable assembly is driven to simultaneously perform the first and second (and optionally the third) movements. Driving the drivable assembly may involve driving the individual joints of the drivable assembly, using the outputs of the inverse kinematics algorithm as computed when determining the first, second, and third movements. The outputs may be joint states (e.g. position and/or orientation, and/or linear or angular velocity or acceleration) used for driving joint actuators (e.g., joint actuators of the first, second and third drivable structures and the first and second tools of the drivable structure of FIG. 1, or joint actuators of the drivable structure, the first and second manipulators, and the first and second tools of the manipulator assembly of FIG. 2B).

As previously noted, the execution of Steps 604, 606, and 608 may involve an inverse kinematics algorithm. Various implementations may exist. For example, in one embodiment, a single inverse kinematics algorithm performs the calculations required by Steps 604, 606, and 608. In another implementation, multiple modularized inverse kinematics algorithms are used. For example, in a modularized robotic system, each of the first, second, and third drivable structures may be controlled by separately executing algorithms. Importantly, while the algorithms may execute separately, they execute in an interdependent manner. For example, the joints involved in the second movement (Step 606) may need to be coordinated with the joints involved in the first movement (Step 604). Further, computations related to determining joint positions and/or orientations of the joints involved in the second movements are performed not only based on a compensation to be performed to cancel the effect of the first movement (Step 606), but also based on the second commanded motion (Step 608).

A supervisory algorithm may coordinate the operation of the modularized inverse kinematics algorithms. Only limited information may be shared with each of the modularized inverse kinematics algorithm. For example, the supervisory algorithm may periodically instruct an inverse kinematics algorithm associated with the first drivable structure and the first tool using cartesian position/orientation commands for the first end effector relative to a base of the first drivable structure (the point where the first drivable structure interfaces with the third drivable structure). The inverse kinematics algorithm may then generate the appropriate commands to drive the joint actuators of the first drivable structure and the first tool. Similarly, the supervisory algorithm may periodically instruct an inverse kinematics algorithm associated with the third drivable structure. Cartesian positional commands may be provided for a distal point of the third drivable structure (where the third drivable structure supports the first drivable structure) relative to a base of the third drivable structure. The inverse kinematics algorithm may then generate the appropriate commands to drive the joint actuators of the third drivable structure, etc.

Steps 600-610 may be repeated until the execution of the method terminates. At least some of the steps are performed at a high rate (e.g., every few milliseconds or faster) to ensure smooth control of the joints involved in the first, second, and third movements.

While the method of FIG. 6 may be used under certain circumstances to coordinate multiple-tool movement, the method is not necessarily always active. For example, the method may not be performed when no first tool is coupled to the first drivable structure, or when no second tool is coupled to the second drivable structure.

In the following paragraphs, additional methods are described. Broadly speaking, the additional methods may be used to detect conditions in which a drivable structure motion, for example, the motion of the first, second, third drivable structure, first tool, and/or second tool, etc., is limited. Depending on which manipulator movement is limited, different outcomes, at least some of them undesirable, may result. The robotic system may respond to the limited motion(s) as subsequently discussed. Also, in any or all of the examples, a status message or other indication of the limitation or response may be provided to the operator.

Each of FIGS. 7A-7D shows a flowchart illustrating a method for responding to a limited motion, in accordance with one or more embodiments. Each of the methods described in conjunction with FIGS. 7A-D may be executed while the method of FIG. 6 is executed. For example, the method of FIGS. 7A, 7B, 7C, and/or 7D may be used to complement the execution of the method of FIG. 6 and respond to certain exceptions.

Figure 7A:
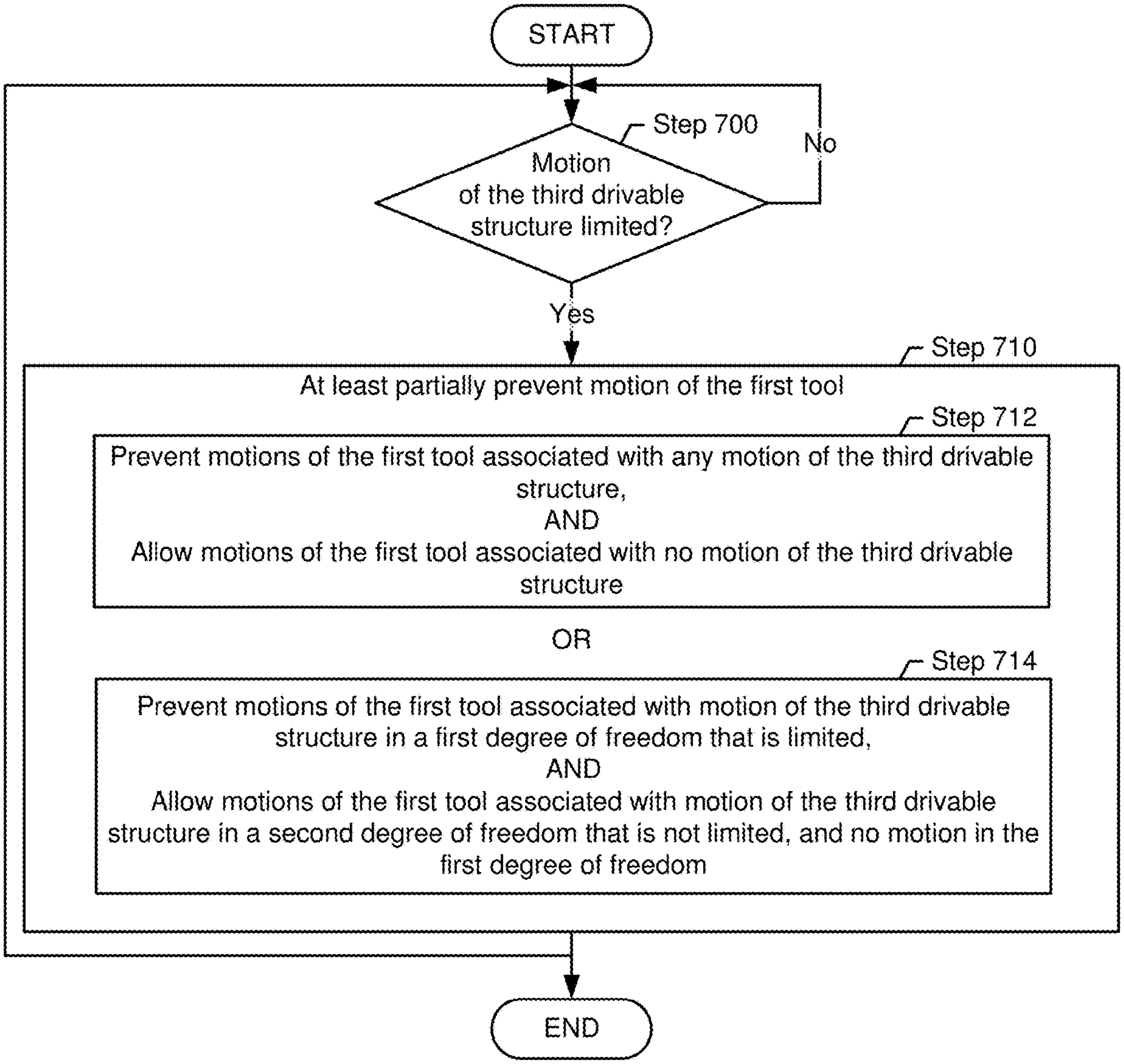
FIG. 7A shows a flowchart describing a method for responding to limited motion, in accordance with one or more embodiments.

Starting with FIG. 7A, in Step 700, referring to the configuration shown in FIG. 1, an evaluation is performed to determine whether motion of the third drivable structure is limited. The evaluation is not limited to the third drivable structure motion determined in Step 604 of FIG. 6, and instead may apply to some or all of the kinds of motion of the third drivable structure. Reasons for the limited motion of the third drivable structure may include, but are not limited to: collisions that have happened or are about to happen, with other manipulators or objects, surpassing a range of motion limit by a current or predicted motion of one or more joints, malfunctioning joint actuators, etc. The evaluation may be performed in various ways. For example, if the workspace in which the third drivable structure operates is known, a simulation may be used to predict a collision for a commanded movement. Having reached or being about to reach a range-of-motion limit may be evaluated based on current joint configurations and known range-of-motion limits. Further, comparing a commanded movement with an actual movement of the drivable assembly may also include an evaluation of if the movement of the third drivable structure is limited. The actual movement may be obtained, for example, using joint parameter sensors. For example, if the actual movement is found to deviate from the commanded movement in any manner or in particular manners, it may be concluded that the movement is limited.

If the evaluation performed in Step 700 indicates that motion of the third drivable structure is limited, the method may proceed with the execution of Step 710. If the evaluation indicates that the motion of the drivable structure is not limited, the method may repeat the execution of Step 700.

While Step 700 has been described with reference to the configuration shown in FIG. 1, the method of FIG. 7 is equally applicable to other embodiments. For example, in the embodiment shown in FIG. 2A, a similar evaluation may be performed for determining if motion of the drivable structure is limited.

In Step 710, motion of the first tool is at least partially prevented. At least partially preventing the motion of the first tool may help avoid unintended outcomes. For example, if the second movement (determined in Step 606) continued while the motion of the third drivable structure is limited, the second end effector may move toward an unintended location. Similarly, the relative positioning between the first and second end effectors may no longer be as intended. Different options for mitigating the limited drivable structure motion are available, as described in Steps 712 and 714. The execution of Steps 700 and 710 in a loop may help ensure that motion of the first tool is at least partially prevented for the duration of the limitation.

In Step 712, motions of the first tool associated with any motion of the (third) drivable structure are prevented, whereas motions of the first tool associated with no motion of the (third) drivable structure are allowed. Accordingly, when motion of the (third) drivable structure is limited, only motions of the first tool that can be performed without motion the (third) drivable structure are allowed. The execution of Step 712 may help ensure that movements are not incompletely performed.

In Step 714, motions of the first tool are prevented where they are associated with limited motion of the (third) drivable structure (the limitation may be in one or more degrees of freedom in Cartesian-space or joint space of the (third) drivable structure.) Accordingly, if a motion of the first tool requires a motion of the (third) drivable structure that cannot be performed, the motion is prevented. Motions of the first tool that are associated with other motions of the (third) drivable structure that are not limited, are allowed. Step 714 thus accommodate more motion of the first tool when motion of the (third) drivable structure is partially limited.

Figure 7B:
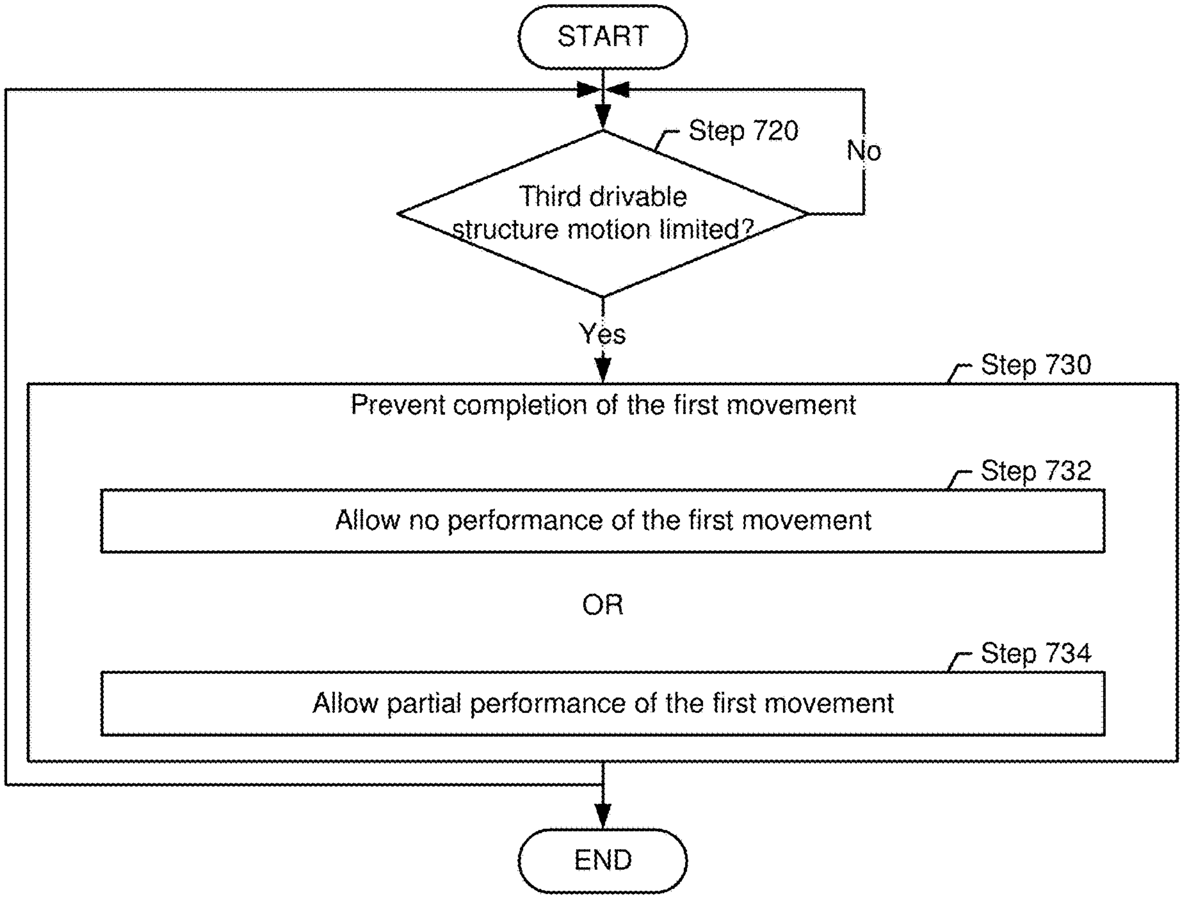
FIG. 7B shows a flowchart describing a method for responding to limited motion, in accordance with one or more embodiments.

Continuing to FIG. 7B, in Step 720, an evaluation is performed to determine whether the third drivable structure motion is limited. Unlike the evaluation in Step 700 of FIG. 7A, the evaluation in Step 720 specifically evaluates the third drivable structure motion determined in Step 604 of FIG. 6, while the evaluation in step 700 evaluates motion of the (third) drivable structure more generally. Reasons for the limited motion of the third drivable structure may include the same reasons as described for FIG. 7A. The evaluation may be performed in various ways, including those described in conjunction with FIG. 7A applied to the third drivable structure motion determined in Step 604. The actual movement may be obtained, for example, using any of the techniques described in conjunction with FIG. 7A.

If the evaluation performed in Step 720 indicates that the third drivable structure motion is limited, the method may proceed with the execution of Step 730. If the evaluation indicates that the third drivable structure motion is not limited, the method may repeat the execution of Step 720.

In Step 730, completion of the first movement is prevented. The execution of Step 730 may help ensure that the movements resulting from the execution of the method of FIG. 6 are not incompletely performed. Different options for preventing completion of the first movement are available, as described in Steps 732 and 734. The execution of Steps 720 and 730 in a loop may help ensure that completion of the first movement is prevented for the duration of the limitation.

In Step 732, no performance of the first movement is allowed. In other words, the execution of the first movement may be entirely prevented.

In Step 734, a partial performance of the first movement may be allowed. Step 734 may allow certain movements, such as movements that do not involve the third drivable structure motion. Example motions that may still be allowed include: an insertion and/or retraction along the insertion axis of the first tool, a pivoting of the first end effector at a wrist joint, and/or an actuation of the end effector (such as an opening and/or closing of jawed end effectors).

In one embodiment, an adjusted first movement is performed instead of the first movement. The adjusted first movement may include anon-limited third drivable structure motion. The adjusted third drivable structure motion is different from the third drivable structure motion in that it can be performed in presence of the limitation. For example, the adjusted third drivable structure motion may involve only joint movement of third drivable structure joints that are non-limited, but not joint movement of third drivable structure joints that are limited. The adjusted third drivable structure motion, as a result, deviates from the limited third drivable structure motion. Thus, the adjusted third drivable structure motion would cause an adjusted second caused motion of the second end effector, instead of the second caused motion associated with the un-adjusted third drivable structure motion. An adjusted second movement is determined to replace the second movement. The adjusted second movement, when performed simultaneously with the adjusted third drivable structure motion, would properly compensate for the adjusted second caused motion. The compensation can be effected when driving the drivable assembly to simultaneously perform the first adjusted movement and the second adjusted movement.

Figure 7C:
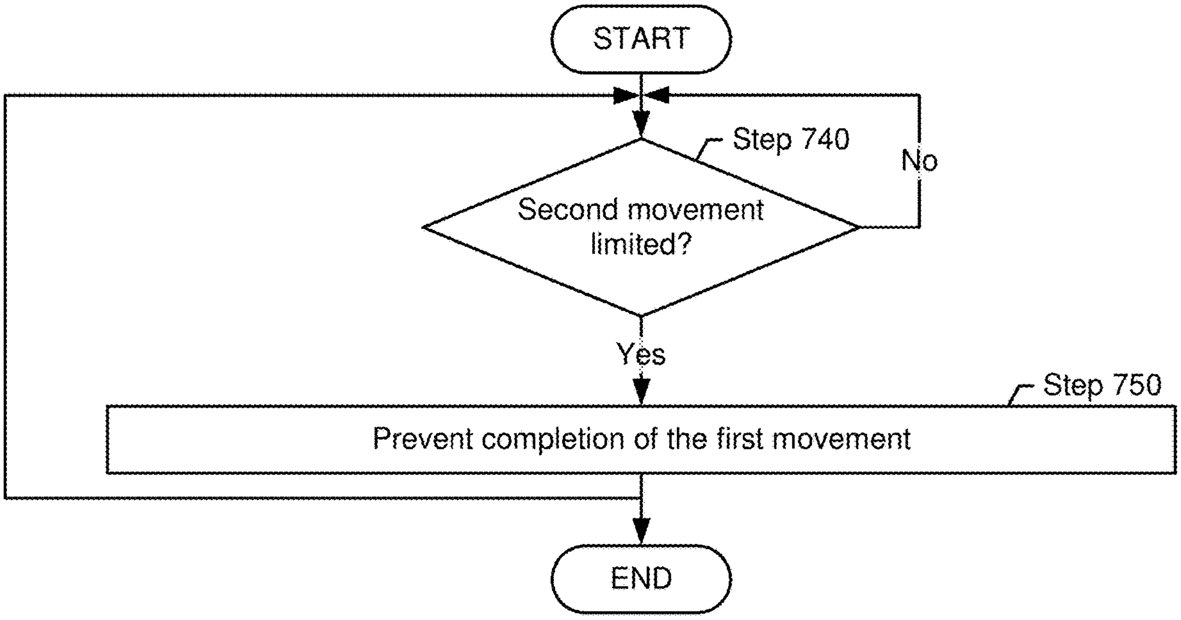
FIG. 7C shows a flowchart describing a method for responding to limited motion, in accordance with one or more embodiments.

Continuing to FIG. 7C, in Step 740, an evaluation is performed to determine whether the second movement, as determined in Step 606 of FIG. 6, is limited. Reasons for the limited second movement may include, but are not limited to collisions that have happened or are about to happen, with other manipulators or objects, surpassing a range of motion limit by a current or predicted motion of one or more joints, malfunctioning joint actuators, etc. The evaluation may be performed in various ways. For example, if the workspace in which the second drivable structure and/or the second tool operates is known, a simulation may be used to predict a collision for a commanded movement. Having reached or being about to reach a range-of-motion limit may be evaluated based on current joint configurations and known range-of-motion limits. Further, comparing a commanded movement with an actual movement of the drivable assembly may also include an evaluation of if the second movement is limited. The actual movement may be obtained, for example, using joint parameter sensors. If the actual movement is found to deviate from the commanded movement in any manner or in particular manners, it may be concluded that the movement is limited.

If the evaluation performed in Step 740 indicates that the second movement is limited, the method may proceed with the execution of Step 750. If the evaluation indicates that the second movement is not limited, the method may repeat the execution of Step 740.

In Step 750, completion of the first movement is prevented. The execution of Step 750 may help ensure that the movements resulting from the execution of the method of FIG. 6 are not incompletely performed. The execution of Steps 740 and 750 in a loop may help ensure that completion of the first movement is prevented for the duration of the limitation.

Figure 7D:
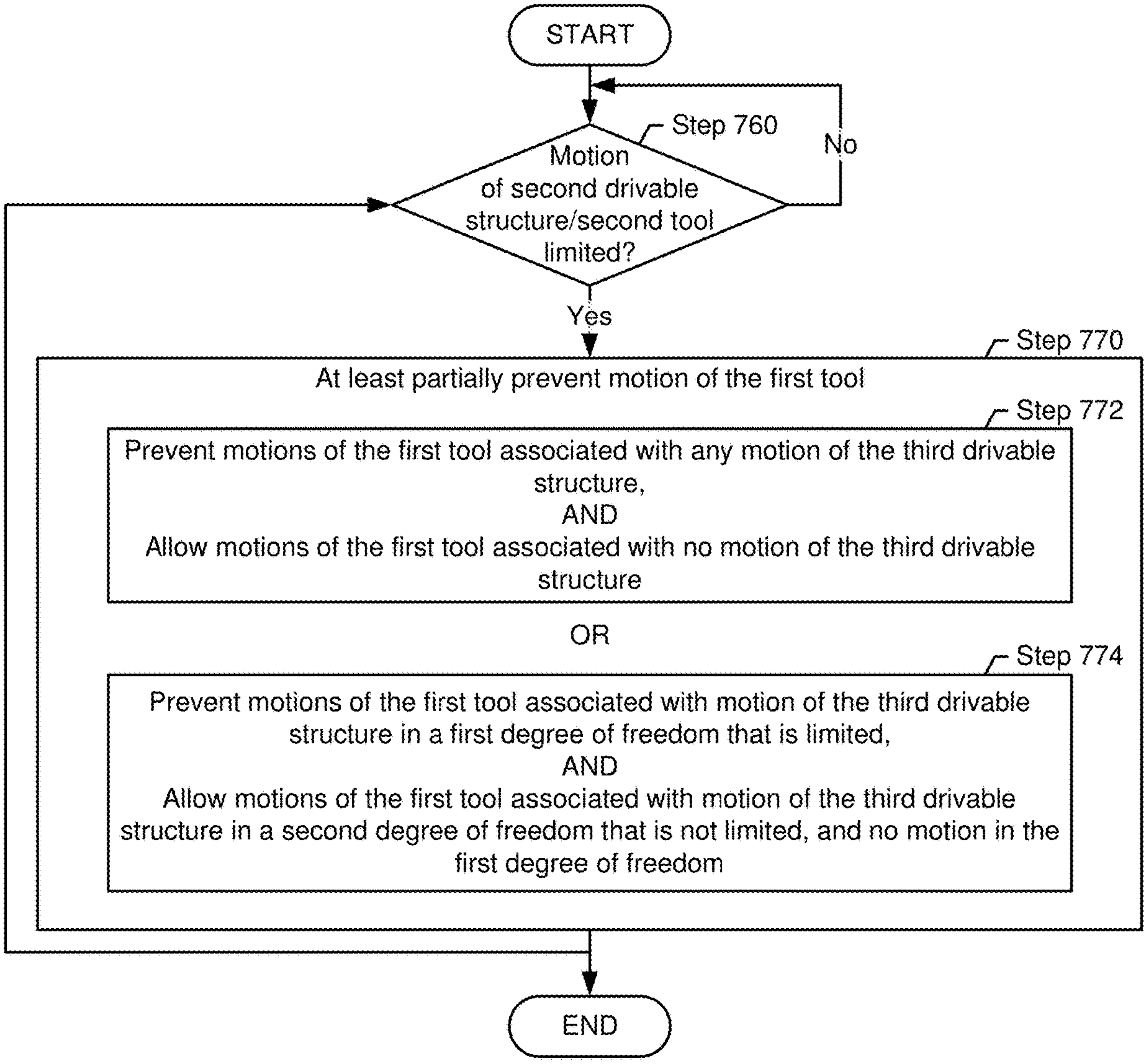
FIG. 7D shows a flowchart describing a method for responding to an limited motion, in accordance with one or more embodiments.

Continuing to FIG. 7D, in Step 760, an evaluation is performed to determine whether motion of the second drivable structure and/or the second tool is limited. The motion of the second drivable structure and/or the second tool may be limited if movement of at least one of the second set of joints is limited. Reasons for the limited motion of the second drivable structure and/or the second tool may include any of the reasons described in conjunction with FIG. 7C. The evaluation may be performed in various ways, including in any of the ways described in conjunction with FIG. 7C. The actual movement may be obtained using any of the techniques described in conjunction with FIG. 7C.

If the evaluation performed in Step 760 indicates that the second movement is limited, the method may proceed with the execution of Step 770. If the evaluation indicates that the second movement is not limited, the method may repeat the execution of Step 760.

In Step 770, motion of the first tool is at least partially prevented. For example, a motion of the first tool is prevented, if that motion of the first tool is associated with motion of the second drivable structure and/or the second tool in a degree of freedom that is limited, whereas other motions of the first tool may be allowed. In other words, motions of the first tool may be allowed as long as they do not involve the limited degrees of freedom of the second drivable structure and/or the second tool. Different options for mitigating the limited second drivable structure and/or second tool motion are available, as described in Steps 772 and 774. The execution of Steps 760 and 770 in a loop may help ensure that motion of the first tool is at least partially prevented for the duration of the limitation.

In Step 772, motions of the first tool associated with any motion of the second drivable structure and/or the second tool (e.g., performed for compensation as previously discussed) are prevented, whereas motions of the first tool associated with no motion of the second drivable structure and/or the second tool are allowed. Accordingly, when motion of the second drivable structure and/or the second tool is limited, only motions of the first tool that can be performed without motion the second drivable structure and/or the second tool are allowed. The execution of Step 712 may help ensure that movements are not incompletely performed.

In Step 774, motions of the first tool are prevented where they are associated with limited motion of the second drivable structure and/or the second tool (the limitation may be in one or more degrees of freedom in Cartesian-space or joint space of the second drivable structure and/or the second tool.) Accordingly, if a motion of the first tool requires a motion of the second drivable structure that cannot be performed, the motion is prevented. Motions of the first tool that are associated with other motions of the second drivable structure that are not limited, are allowed. Step 774 thus accommodate more motion of the first tool when motion of the second drivable structure is partially limited.

While the flowcharts of FIG. 7A, FIG. 7B, FIG. 7C, and FIG. 7D discuss responses to limitations associated with the second or the third drivable structures, those skilled in the art will appreciate that limitations associated with the first drivable structure (or any other drivable structure of the robotic system) may be handled in a similar manner.

Figure 8:
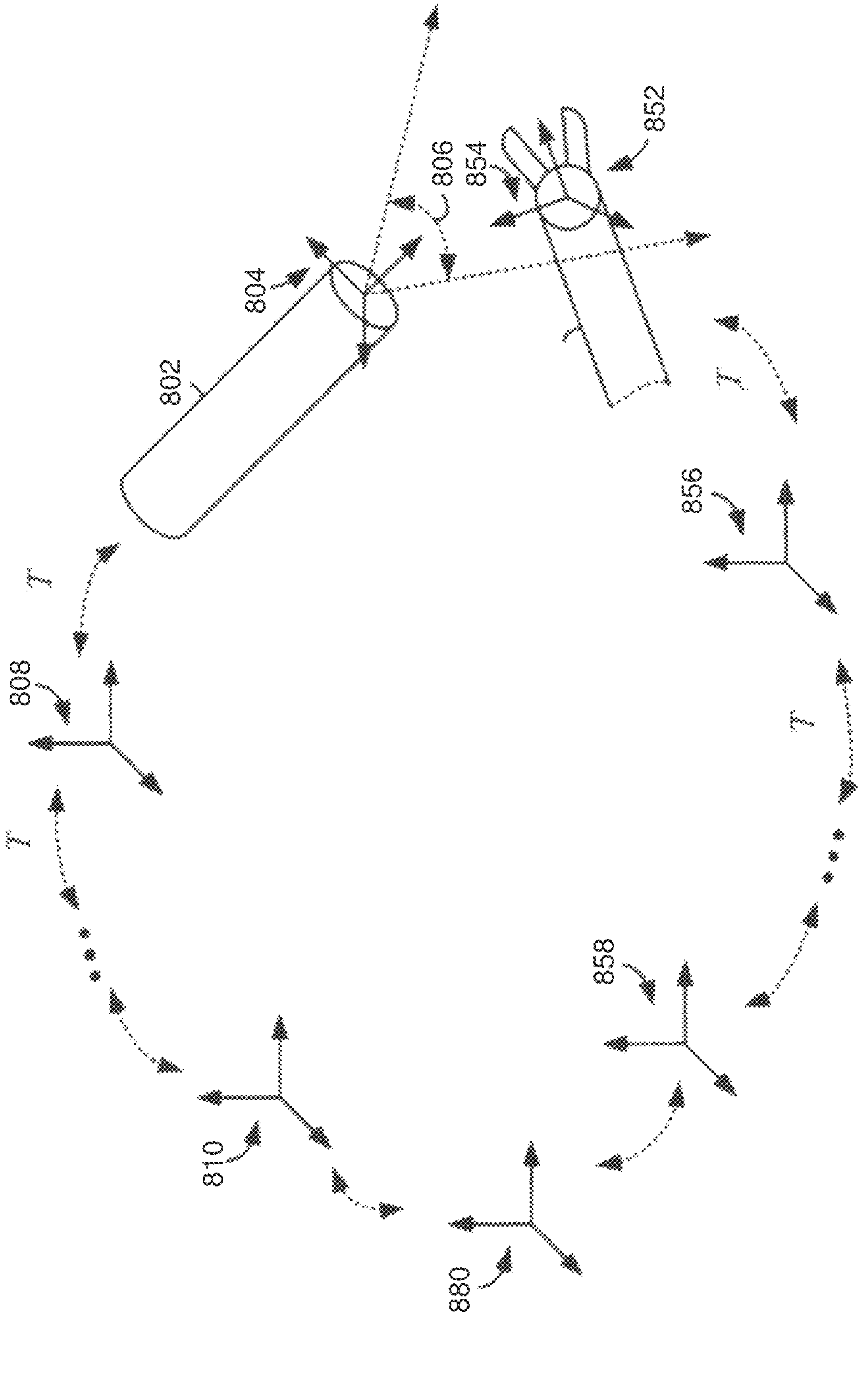
FIG. 8 shows transformations between reference frames, in accordance with one or more embodiments.

Turning to FIG. 8, transformations between reference frames, in accordance with one or more embodiments, are shown. As noted for some embodiments above, in one or more embodiments, commanded motions (e.g., of end effectors) are provided relative to an imaging reference frame of an imaging device.

In some embodiments where commanded motions are provided relative to an imaging reference frame of an imaging device, the methods used for controlling end effectors of tools cause end effector orientational and positional movement as viewed in the image of the display unit (254) of FIG. 2A. Such movements are mapped onto orientational and positional movement of the input device(s) (252), as subsequently described.

In the following description, a single input device is associated with a single end effector of a tool. The input device is subsequently referred to as "leader" and the associated manipulator arm and tool is referred to as "follower." Such systems have commonly been known in the industry as teleoperation systems, or master-slave systems, with the input device being referred to as the "master", and the associated manipulator arm and tool being referred to as the "slave".

Control between leader and follower movement is achieved by comparing leader position and orientation in an eye Cartesian coordinate reference system (also referred to herein as the "eye reference frame") with follower position and orientation in a camera Cartesian coordinate reference system (also referred to herein as the "imaging reference frame"). Accordingly, when the leader is stationary, the follower position and orientation within the imaging reference frame is compared with the leader position and orientation in the eye reference frame, and if the position and/or orientation of the follower in the imaging reference frame does not correspond with the position and/or orientation of the leader in the eye reference frame, the follower is caused to move to a position and/or orientation in the imaging reference frame at which its position and/or orientation in the imaging reference frame does correspond with the position and/or orientation of the leader in the eye reference frame.

When the leader is moved into a new position and/or orientation in the eye reference frame, the new leader position and/or orientation does not correspond with the previously corresponding follower position and/or orientation in the imaging reference frame. The control methods may then cause the follower to move into a new position and/or orientation in the imaging reference frame at which position and orientation in the imaging reference frame do correspond with the new position and/or orientation of the leader in the eye reference frame.

In this control paradigm, the control of a tool in response to operator manipulation of a leader control device may rely on a number of additional definable reference frames and corresponding frame transforms to map points in one frame to corresponding points in another frame, as subsequently discussed with reference to FIG. 8.

FIG. 8 shows a generalized example of such reference frames and corresponding transforms. Specially, the illustration of FIG. 8 is used to illustrate the representation of an end effector (652) with an end effector reference frame (854) in an imaging reference frame (804). The end effector reference frame (854) is of an end effector of a first tool, and the imaging reference frame is of a second tool including an imaging device (802). The imaging device (802) has field of view (806). The representation of the end effector (852) in the imaging reference frame (804) may be accomplished by a mapping using the homogenous transform $$^{Camera}_{Tool}T.$$

The homogenous transform may be a 4×4 matrix including elements describing the translational and rotational components of the transform. The transform $$^{Camera}_{Tool}T,$$

as generally illustrated in FIG. 8 may be broken up into series of transforms, including intermediate transforms via intermediate reference frames (808, 810) between the reference frame (804) of the imaging device (802) and a base reference frame or world reference frame (880), and additional intermediate transforms via intermediate reference frames (856, 858) between the end effector reference frame (654) of the end effector (852) and the base or world reference frame (880). The transform $$^{Camera}_{Tool}T$$

may thus be accomplished in a stepwise manner via a series of sequentially performed transforms.

Referring to the example introduced in FIG. 5A and FIG. 5B, $$^{Camera}_{Tool}T$$

may be defined as a series of transforms between the camera reference frame, attached to the imaging device (518) and the tool reference frame attached to the end effector (512) via a reference frame attached to the manipulator-supporting link (502). The reference frame attached to the manipulator-supporting link (502) may, thus, correspond to the base reference frame (880) in FIG. 8. Multiple intermediate reference frames may be attached to the links of the tool (510) and the tool (516), with intermediate transforms linking these reference frames. Additional reference frames may further be established for the tool (504). While in the example of FIG. 5A and FIG. 5B, it may be sufficient to attach the base reference frame to the manipulator-supporting link (502) to enable the end effector to be represented in the imaging reference frame of the imaging device, the base reference frame may alternatively be placed elsewhere, without departing from the disclosure. For example, the base reference frame may be attached to the base (212) of the robotic manipulator assembly (210) of FIG. 2A, with multiple transforms along the links (214, 220), and/or the drivable structure (222). Depending on how control algorithms, e.g., the inverse kinematics control algorithms used to determine the joint positions and/or orientations, are modularized, different choices of reference frames may be advantageous.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A robotic system comprising:

a drivable assembly comprising:

a first drivable structure configured to support and move a first tool;

a second drivable structure configured to support and move a second tool, the second tool comprising an imaging device, wherein the second drivable structure and the second tool together comprise a plurality of second links coupled by a plurality of second joints;

a third drivable structure mechanically coupled to the first drivable structure and mechanically coupled to the second drivable structure, such that moving the third drivable structure moves proximal portions of the first and second drivable structures; and a processing system configured to perform operations comprising:

receiving a command from an input device, the command indicating a commanded motion for a first end effector of the first tool relative to an imaging reference frame of the imaging device, determining a first movement of the drivable assembly for effecting the commanded motion, the first movement comprising a third drivable structure motion of the third drivable structure, determining a second movement of the plurality of second joints to compensate for an effect of the third drivable structure motion on the imaging reference frame and maintain a state of the imaging reference frame relative to a world reference frame, and driving the drivable assembly to simultaneously perform the first and second movements.

2. The robotic system of claim 1, wherein the drivable assembly further comprises:

an additional drivable structure mechanically coupled to the third drivable structure, the additional drivable structure configured to support and move an additional tool with an additional end effector, wherein the additional drivable structure and the additional tool together comprise a plurality of additional links coupled by a plurality of additional joints; and wherein the operations further comprise:

determining an additional movement of the plurality of additional joints, wherein performing the additional movement simultaneously with the third drivable structure motion would maintain a state of the additional end effector, and driving the drivable assembly with the additional movement to simultaneously perform the first movement, second movement, and additional movement.

3. The robotic system of claim 2, wherein the operations further comprise:

receiving a further command, the further command indicating a further commanded motion for the additional end effector, determining further movement of the plurality of additional joints, wherein the further movement is for effecting the further commanded motion when performed simultaneously with the third drivable structure motion and the additional movement, and driving the drivable assembly with the further movement to simultaneously perform the first, second, additional, and further movements.

4. The robotic system of claim 1, wherein the operations further comprise:

determining whether a motion of the third drivable structure is limited; and at least partially preventing motion of the first tool while the motion of the third drivable structure is determined to be limited.

5. The robotic system of claim 1, wherein the operations further comprise:

determining whether a motion of the third drivable structure is limited; and preventing a completion of the first movement in response to determining that the motion of the third drivable structure is limited.

6. The robotic system of claim 5, wherein preventing the completion of the first movement comprises:

disallowing performance of the first movement.

7. The robotic system of claim 5, wherein preventing the completion of the first movement comprises:

allowing partial performance of the first movement.

8. The robotic system of claim 1, wherein the operations further comprise:

not allowing the imaging reference frame to move with the third drivable structure while the first tool is coupled to the robotic system; and allowing the imaging reference frame to move with the third drivable structure when the first tool is not coupled to the robotic system.

9. The robotic system of claim 1, wherein the operations further comprise:

determining whether a motion of the plurality of second joints is limited; and at least partially preventing a motion of the first tool while the motion of the plurality of second joints is determined to be limited.

10. The robotic system of claim 9, wherein at least partially preventing motion of the first tool comprises:

preventing motions of the first tool associated with any motion of the plurality of second joints; and allowing motions of the first tool associated with no motion of the plurality of second joints.

11. The robotic system of claim 9, wherein in response to the motion of the plurality of second joints being limited by being limited in a first degree of freedom and not being limited in a second degree of freedom, at least partially preventing motion of the first tool comprises:

preventing motions of the first tool associated with motion of the plurality of second joints in the first degree of freedom; and allowing motions of the first tool associated with motion of the plurality of second joints in the second degree of freedom.

12. A method for operating a drivable assembly of a robotic system, the drivable assembly comprising:

a first drivable structure configured to support and move a first tool;

a second drivable structure configured to support and move a second tool, the second tool comprising an imaging device, wherein the second drivable structure and the second tool together comprise a plurality of second links coupled by a plurality of second joints, a third drivable structure mechanically coupled to the first drivable structure and mechanically coupled to the second drivable structure, such that moving the third drivable structure moves proximal portions of the first and second drivable structures; and the method comprising:

receiving a command from an input device, the command indicating a commanded motion for a first end effector of the first tool relative to an imaging reference frame of the imaging device, determining a first movement of the drivable assembly for effecting the commanded motion, the first movement comprising a third drivable structure motion of the third drivable structure, determining a second movement of the plurality of second joints to compensate for an effect of the third drivable structure motion on the imaging reference frame and maintain a state of the imaging reference frame relative to a world reference frame, and driving the drivable assembly to simultaneously perform the first and second movements.

13. The method of claim 12, further comprising:

determining whether a motion of the third drivable structure is limited; and at least partially preventing motion of the first tool while the motion of the third drivable structure is determined to be limited.

14. The method of claim 12, further comprising:

determining whether a motion of the third drivable structure is limited; and preventing a completion of the first movement in response to determining that the motion of the third drivable structure is limited.

15. The method of claim 12, further comprising:

not allowing the imaging reference frame to move with the third drivable structure while the first tool is coupled to the robotic system; and allowing the imaging reference frame to move with the third drivable structure when the first tool is not coupled to the robotic system.

16. The method of claim 12, further comprising:

determining whether a motion of the plurality of second joints is limited; and at least partially preventing a motion of the first tool while the motion of the plurality of second joints is determined to be limited.

17. The method of claim 16, wherein at least partially preventing motion of the first tool comprises:

preventing motions of the first tool associated with any motion of the plurality of second joints; and allowing motions of the first tool associated with no motion of the plurality of second joints.

18. The method of claim 16, wherein in response to the motion of the plurality of second joints being limited by being limited in a first degree of freedom and not being limited in a second degree of freedom, at least partially preventing motion of the first tool comprises:

preventing motions of the first tool associated with motion of the plurality of second joints in the first degree of freedom; and allowing motions of the first tool associated with motion of the plurality of second joints in the second degree of freedom.

19. A non-transitory computer readable medium comprising a plurality of computer-readable instructions which, when executed by one or more processors associated with a drivable assembly, cause the one or more processors to perform a method comprising:

receiving a command from an input device, the command indicating a commanded motion for a first end effector of a first tool relative to an imaging reference frame of an imaging device;

determining a first movement of a drivable assembly for effecting the commanded motion, the first movement comprising a third drivable structure motion of a third drivable structure;

determining a second movement of a plurality of second joints to compensate for an effect of the third drivable structure motion on the imaging reference frame and maintain a state of the imaging reference frame relative to a world reference frame; and driving the drivable assembly to simultaneously perform the first and second movements;

wherein the drivable assembly comprises:

a first drivable structure, wherein the first drivable structure is configured to support and move the first tool;

a second drivable structure configured to support and move a second tool, the second tool comprising the imaging device, wherein the second drivable structure and the second tool together comprise a plurality of second links coupled by the plurality of second joints; and the third drivable structure, wherein the third drivable structure is mechanically coupled to the first drivable structure and mechanically coupled to the second drivable structure, such that moving the third drivable structure moves proximal portions of the first and second drivable structures.

20. The non-transitory computer readable medium of claim 19, wherein the method further comprises:

determining that a motion of the third drivable structure is limited; and at least partially preventing motion of the first tool while the motion of the third drivable structure is determined to be limited.

* * * * *